(12) United States Patent
Timans

(10) Patent No.: US 7,393,530 B2
(45) Date of Patent: Jul. 1, 2008

(54) IL-1-LIKE CYTOKINE ANTIBODIES

(75) Inventor: Jacqueline C. Timans, Mountain View, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/483,312

(22) Filed: Jul. 7, 2006

(65) Prior Publication Data
US 2007/0128195 A1    Jun. 7, 2007

Related U.S. Application Data

(62) Division of application No. 10/695,195, filed on Oct. 27, 2003, now Pat. No. 7,108,850, which is a division of application No. 09/398,412, filed on Sep. 17, 1999, now Pat. No. 6,680,380.

(60) Provisional application No. 60/100,948, filed on Sep. 18, 1998.

(51) Int. Cl.
*G01N 33/53* (2006.01)
*G01N 33/567* (2006.01)
*C07K 16/24* (2006.01)
*A61K 39/395* (2006.01)

(52) U.S. Cl. .............. 424/139.1; 424/141.1; 424/145.1; 435/7.1; 435/810; 435/975; 530/387.9; 530/388.1; 530/388.15

(58) Field of Classification Search .................. None
See application file for complete search history.

(56) References Cited

U.S. PATENT DOCUMENTS

| 5,194,596 A | 3/1993 | Tischer et al. |
| 6,117,654 A | 9/2000 | Pan |
| 7,033,783 B2 | 4/2006 | Sims et al. |

FOREIGN PATENT DOCUMENTS

| EP | 0 541 920 A1 | 5/1993 |
| EP | 0 855 404 A1 | 7/1998 |
| WO | WO 99/06426 | 2/1999 |
| WO | WO 99/07850 | 2/1999 |
| WO | WO 99/36541 | 7/1999 |

OTHER PUBLICATIONS

Arnon and Van Regenmortel, (1992) *The FASEB Journal* 6:3265-3274 "Structural basis of antigenic specificity and design of new vaccines".
Auron, et al., GenPept, Accession No. 124303, Jul. 15, 1998. Definition: Interleukin-1 Beta Precursor (IL-1 Beta) (Catabolin).
Bancroft, et al., Immunol. Reviews, 124:5-24, 1991. "Natural Immunity: A T-Cell-Independent Pathway of Macrophage Activation, Defined in the scid Mouse".
Bazan, et al., Nature, 379:591, Feb. 15, 1996. "A newly defined interleukin-1?".
Belvin, et al., Annu. Rev. Cell Dev. Biol., 12:393-416, 1996. "A conserved signaling pathway; The Drosophila TollDorsal Pathway".
Benjamin, et al. (1998) *Development* 125:1591-1598 "A plasticity window for blodd vessel remodeling is defined by pericyte coverage of the preformed endothelial network and is regulated by PDGF-B and VEGF".
Carrier, GenBank, Accession No. X64532, Jun. 25, 1997. Definition: "H.sapiens gene for interleukin-1 receptor antagonist".
Carter, et al., GenPept, Accession No. 124312, Jul. 15, 1998. Definition: Interleukin-1 receptor antagonist protein precursor (IL-1RA) (ICIL-1RA) (IRAP).
Cominelli, et al., J. Biol. Chem., 296(9):6962-6971, Mar. 4, 1994. "Rabbit Interleukin-1 Receptor Antagonist".
Cominelli, et al., GenBank, Accession No. S68977, Sep. 22, 1994. Definition: "sIL-1ra=interleukin-1 receptor antagonist secreted form [rabbits, colon tissue, mRNA, 574 nt.]".
Dinarello, Blood, 77(8):1638-1652, Apr. 15, 1991. "Interleukin-1 and Interleukin-Antagonism".
Dinarello, The FASEB Journal, 8:1314-1325, Dec. 1994. "The interleukin-1 family: 10 years of discovery".
Dinarello, Blood, 87(6):2095-2147, Mar. 15, 1996. "Biologic Basis for interleukin-1 in Disease".
Gao, W., et al. (2003) *J. Immunol.* 170:107-113 "Innate Immunity Mediated by the Cytokine IL-1 Homologue 4 (IL-1H4/IL-1F7) Induces IL-12-Dependent Adaptive and Profound Antitumor Immunity".
Gilmore, et al., GenBank, Accession No. Z70047, Mar. 11, 1996. Definition: "C.familiaris mRNA for interleukin-1 beta".
Goto, et al., GenBank, Accession No. D21832, Apr. 21, 1994. Definition: "Rabbit mRNA for interleukin-1 receptor antagonist, complete cds."
Gronenborn and Clore, Protein Engineering, 4(3):263-269, 1991. "Modeling the three-dimensional structure of the monocyte chemoattractant and activating protein MCAF/MCP-1 on the basis of the solution structure of interleukin-8".
Hamada and Mulligan, et al., GenBank, Accession No. M57526, Jan. 30, 1992. Definition: "Rabbit interleukin-1 receptor antagonist (IL1RA) mRNA, complete cds."
Hanks, et al., Methods in Enzymology, 2000:38-62, 1991. "[2] Protein Kinase Catalytic Domain Sequence Database: Identification of Conserved Features of Primary Structure and Classification of Family Members".
Hannon, et al., GenBank, Accession No. I09591, Nov. 14, 1994. Definition: "Sequence 1 from Patent WO 8911540".
Hannon, et al., GenBank, Accession No. I09592, Nov. 14, 1994. Definition: "Sequence 3 from Patent WO 8911540".
Hultmark, Nature, 367:116-117, Jan. 13, 1994. "Ancient Relationships".

(Continued)

*Primary Examiner*—Prema Mertz
(74) *Attorney, Agent, or Firm*—Edwin P. Ching; Gregory R. Bellomy

(57) ABSTRACT

Nucleic acids encoding mammalian, e.g., primate, IL-1ζ, purified IL-1ζ polypeptides and fragments thereof. Binding proteins, e.g., antibodies, both polyclonal and monoclonal, are also provided. Methods of using the compositions for both diagnostic and therapeutic utilities are provided.

11 Claims, No Drawings

OTHER PUBLICATIONS

Hunter, et al., J. Immunology, 155:4347-4345, 1995. "IL-1β Is Required for IL-12 to induce Production of IFN-γ by NK Cells. A Role for IL-1β in the T Cell-Independent Mechanism of Resistance Against Intracellular Pathogens."

Jenkins, et al., GenBank, Accession No. U65590, Dec. 22, 1997. Definition: "*Homo sapiens* IL-1 receptor antagonist IL-1Ra (IL-1RN) gene, alternatively spliced forms, complete cds."

Kumar, S., et al, GenBank, Locus Q9NZH6, 218 aa, linear, PRI Jan. 24, 2006 Definition: Interleukin-1 family member 7 precursor (IL-1F7) (Interleukin-1 zeta) (IL-1 zeta) (FIL1 zeta) (Interleukin-1 homolog 4) (IL-1H4) (Interleukin-1-related protein) (IL-1RP1) (IL-1X protein).

Kumar, et al. (2000) *J. Biol. Chem.* 275:10308-10314 "Identification and initial characterization of four novel members of the interleukin-1 family".

Lemaitre, et al., Cell, 86:973-983, Sep. 20, 1996. "The Dorsoventral Regulatory Gene Cassette spätzle/Toll/cactus Controls the Potent Antifungal Response in Drosphila Adults".

Leong, GenBank, Accession No. X12497, Mar. 13, 1995. Definition: "Bovine mRNA for interleukin-1 alpha".

Lodi, et al., Science, 263:1762-1767, Mar. 25, 1994. "High-Resolution Structure of the β Chemokine hMIP-1β by Multidimensional NMR".

Maliszewski, GenBank, Accession No. X52731, Mar. 31, 1995. Definition: "Pig mRNA for interleukin 1-alpha".

March, et al., GenPept, Accession No. 124297, Oct. 1, 1996. Definition: "Interleukin-1 alpha precursor (IL-1 alpha (hematopoietin-1))".

Marra, et al., GenBank, Accession No. AA030324, Jan. 21, 1997. Definition: "mi08c10.r1 Soares mouse placenta 4NbMP13.5 14.5 Mus musculus cDNA clone 459858 5', mRNA sequence".

Marra, et al., GenBank, Accession No. W08205, Sep. 5, 1996. Definition: "mb49b11.r1 Soares mouse p3NMF19.5 Mus musculus cDNA clone 332733 5' similar to PIR:A49031 A49031 interleukin 1 receptor antagonist—mouse ; mRNA sequence".

Masaaki, et al., GenBank, Accession No. E01109, Nov. 26, 1996. Definition: "cDNA sequence of human IL-1".

Masaaki, et al., GenBank, Accession No. E01442, Nov. 26, 1996. Definition: "cDNA encoding human IL-1".

McMahan, et al., The EMBO Journal, 10(10):2821-2832, Oct. 1991. "A novel IL-1 receptor, cloned from B cells by mammalian expression, is expressed in many cell types".

Morisato and Anderson, Annu. Rev. Genetics, 29:371-399, 1995. "Signaling pathways that establish the dorsal-ventral pattern of the Drosophilia embryo".

Nishida, et al., GenBank, Accession No. D00403, Jan. 19, 1992. Definition: "Rat interleukin-1 alpha mRNA, complete cds."

Okamura, et al., Nature, 378:88-91, Nov. 2, 1995. "Cloning of a new cytokine that induces IFN-g production by T cells".

Oppenheim, et al., Ann. Rev. Immunol. 9:617-648, 1991, "Properties of the novel proinflammatory supergene 'intercrine' cytokine family".

Parker, et al., Nature, 363:736-738, Jun. 24, 1993. "Phosphorylation and inactivation of the mitotic inhibitor Wee1 by the nim1/cdr1 kinase".

Rothe, et al., The Journal of Clinical Investigation, 99(3):469-474, Feb. 1997. "Active Stage of Autoimmune Diabetes Is Associated with the Expression of a Novel Cytokine, IGIF, Which Is Located Near Idd2".

Sayle and Milner-White, TIBS, 20:374-376, Sep. 1995. "Rasmol: biomolecular graphics for all".

Seow, GenBank, Accession No. X56972, May 26, 1992. Definition: "Ovine IL-1 beta mRNA for interleukin-1 beta".

Skolnick, et al. (2000) *Nature Biotechnology* 18:283-287 "Structural genomics and its importance for gene function analysis".

Smith, et al. J. Biol. Chem. 275(2):1169-1175, Jan. 14, 2000. "Four new members expand the interleukin-1 superfamily".

Storkus, W.J., et al. "Interleukin-12" in: Thomson, *The Cytokine Handbook*, (3rd ed., Academic Press, 1998) pp. 391-425. ISBN 0-12-689662-3.

Stratagene Catalog, 1988, p. 39.

Strausberg (NCI-CGAP), GenBank, Accession No. AI014548, Aug. 27, 1998. Definition: "ou40f01.x1 Soares_NFL_T_GBC_S1 *Homo sapiens* cDNA clone Image:1628761 3', mRNA sequence."

Telford, et al., GenBank, Accession No. X04964, Sep. 16, 1994. Definition: "Murine interleukin-1 beta gene".

Thompson, et al., Nucleic Acids Research, 25(24):4876-4882, 1997. "The Clustal_X windows interface: flexible strategies for multiple sequence alignment aided by quality analysis tools."

Totsuka, et al., GenBank, Accession No. D63353, Feb. 13, 1997. Definition: "Cynomolgus monkey mRNA for interleukin-1-beta".

Tribbick, G. (2002) *J. Immunol. Methods* 267:27-35 "Multipin peptide libraries for antibody and receptor epitope screening and characterization".

Ushio, et al., GenPept, Accession No. 1405319, Jul. 5, 1996. Definition: "interferon-gamma inducing factor (IGIF)".

Vukicevic, et al. (1996) *PNAS USA* 93:9021-9026 "Induction of nephrogenic mesenchyme by osteogenic protein 1 (bone morphogenetic protein 7)".

Zahedi, et al., GenBank, Accession No. M74294, Aug. 23, 1991. Definition: "Mouse IL-1m antagonist protein mRNA, complete cds."

```
                           SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
        (A) LENGTH: 1225 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 491..1144

(xi) SEQUENCE DESCRIPTION: SEQ ID NO: 1:

CGGTTTGTTT TCTTTAGAGA TTTTACAGTG TTGGTTATAA TTGTGCACTT AATCTTTATT      60

TTCCTTATAC AGTAGTCCCC CCGATCAACT GGGGGCATGT TCCATACCCC TGGTGGATTC     120

CTGAAACTGC CAGTTAGTAC CAAACCCTAT ATAGATTGTG TTTTTTCCTG TACGCAGGCC     180

GACACACAGG AAATCATAAG TCAGGAGGGC CACTGCCACG CAGGAAAGAC CCATCTGAAC     240

TGCTGCAAAA GCTCCGTGTC GATTTATTGC TTCCACAAAT AGTGCCGATA TGCACCAGGC     300

ACTGTTGTAA AACTGAAAAT ATGTTTTGGG ATGTGCCCAG TCTACCTAGC TCCTTCAAGT     360

AAAGGATCCT GAGAACTGAA GGCAAACAGA GCTCCAGGAG TCCAAGACAG AGCCACACAC     420

CACGAGGATC CTGGCCCAGG TCTTGGACTT CCATTCCCAT TTCTGTTGAG TAATAAACTC     480

AACGTTGAAA ATG TCC TTT GTG GGG GAG AAC TCA GGA GTG AAA ATG GGC       529
             Met Ser Phe Val Gly Glu Asn Ser Gly Val Lys Met Gly
               1               5                  10

TCT GAG GAC TGG GAA AAA GAT GAA CCC CAG TGC TGC TTA GAA GAC CCG       577
Ser Glu Asp Trp Glu Lys Asp Glu Pro Gln Cys Cys Leu Glu Asp Pro
    15                  20                  25

GCT GGA AGC CCC CTG GAA CCA GGC CCA AGC CTC CCC ACC ATG AAT TTT       625
Ala Gly Ser Pro Leu Glu Pro Gly Pro Ser Leu Pro Thr Met Asn Phe
 30                  35                  40                  45

GTT CAC ACA AGT CGA AAG GTG AAG AGC TTA AAC CCG AAG AAA TTC AGC       673
Val His Thr Ser Arg Lys Val Lys Ser Leu Asn Pro Lys Lys Phe Ser
                 50                  55                  60
```

```
ATT CAT GAC CAG GAT CAC AAA GTA CTG GTC CTG GAC TCT GGG AAT CTC       721
Ile His Asp Gln Asp His Lys Val Leu Val Leu Asp Ser Gly Asn Leu
            65                  70                  75

ATA GCA GTT CCA GAT AAA AAC TAC ATA CGC CCA GAG ATC TTC TTT GCA       769
Ile Ala Val Pro Asp Lys Asn Tyr Ile Arg Pro Glu Ile Phe Phe Ala
        80                  85                  90

TTA GCC TCA TCC TTG AGC TCA GCC TCT GCG GAG AAA GGA AGT CTG ATT       817
Leu Ala Ser Ser Leu Ser Ser Ala Ser Ala Glu Lys Gly Ser Leu Ile
    95                 100                 105

CTC CTG GGG GTC TCT AAA GGG GAG TTT TGT CTC TAC TGT GAC AAG GAT       865
Leu Leu Gly Val Ser Lys Gly Glu Phe Cys Leu Tyr Cys Asp Lys Asp
110                 115                 120                 125

AAA GGA CAA AGT CAT CCA TCC CTT CAG CTG AAG AAG GAG AAA CTG ATG       913
Lys Gly Gln Ser His Pro Ser Leu Gln Leu Lys Lys Glu Lys Leu Met
                130                 135                 140

AAG CTG GCT GCC CAA AAG GAA TCA GCA CGC CGG CCC TTC ATC TTT TAT       961
Lys Leu Ala Ala Gln Lys Glu Ser Ala Arg Arg Pro Phe Ile Phe Tyr
            145                 150                 155

AGG GCT CAG GTG GGC TCC CGG AAC ATG CTG GAG TCG GCG GCT CAC CCC      1009
Arg Ala Gln Val Gly Ser Arg Asn Met Leu Glu Ser Ala Ala His Pro
        160                 165                 170

GGA TGG TTC ATC TGC ACC TCC TGC AAT TGT AAT GAG CCT GTT GGG GTG      1057
Gly Trp Phe Ile Cys Thr Ser Cys Asn Cys Asn Glu Pro Val Gly Val
    175                 180                 185

ACA GAT AAA TTT GAG AAC AGG AAA CAC ATT GAA TTT TCA TTT CAA CCA      1105
Thr Asp Lys Phe Glu Asn Arg Lys His Ile Glu Phe Ser Phe Gln Pro
190                 195                 200                 205

GTT TGC AAA GCT GAA ATG AGC CCC AGT GAG GTC AGC GAT TAGGAAACTG       1154
Val Cys Lys Ala Glu Met Ser Pro Ser Glu Val Ser Asp
                210                 215

CCCCATTGAA CGCCTTCCTC GCTAATTTGA ACTAATTGTA TAAAACCCC AAACCTGC       1214

ACTAAAAAAA A                                                         1225

(2) INFORMATION FOR SEQ ID NO: 2:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO: 2:

Met Ser Phe Val Gly Glu Asn Ser Gly Val Lys Met Gly Ser Glu Asp
 1               5                  10                  15

Trp Glu Lys Asp Glu Pro Gln Cys Cys Leu Glu Asp Pro Ala Gly Ser
            20                  25                  30

Pro Leu Glu Pro Gly Pro Ser Leu Pro Thr Met Asn Phe Val His Thr
        35                  40                  45

Ser Arg Lys Val Lys Ser Leu Asn Pro Lys Lys Phe Ser Ile His Asp
    50                  55                  60

Gln Asp His Lys Val Leu Val Leu Asp Ser Gly Asn Leu Ile Ala Val
65                  70                  75                  80

Pro Asp Lys Asn Tyr Ile Arg Pro Glu Ile Phe Phe Ala Leu Ala Ser
                85                  90                  95

Ser Leu Ser Ser Ala Ser Ala Glu Lys Gly Ser Leu Ile Leu Leu Gly
            100                 105                 110

Val Ser Lys Gly Glu Phe Cys Leu Tyr Cys Asp Lys Asp Lys Gly Gln
        115                 120                 125
```

```
Ser His Pro Ser Leu Gln Leu Lys Lys Glu Lys Leu Met Lys Leu Ala
    130                 135                 140
Ala Gln Lys Glu Ser Ala Arg Arg Pro Phe Ile Phe Tyr Arg Ala Gln
145                 150                 155                 160
Val Gly Ser Arg Asn Met Leu Glu Ser Ala Ala His Pro Gly Trp Phe
                165                 170                 175
Ile Cys Thr Ser Cys Asn Cys Asn Glu Pro Val Gly Val Thr Asp Lys
                180                 185                 190
Phe Glu Asn Arg Lys His Ile Glu Phe Ser Phe Gln Pro Val Cys Lys
                195                 200                 205
Ala Glu Met Ser Pro Ser Glu Val Ser Asp
210                 215
```

(2) INFORMATION FOR SEQ ID NO: 3:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..654

(xi) SEQUENCE DESCRIPTION: SEQ ID NO: 3:

```
ATG TCC TTT GTG GGG GAG AAC TCA GGA GTG AAA ATG GGC TCT GAG GAC    48
Met Ser Phe Val Gly Glu Asn Ser Gly Val Lys Met Gly Ser Glu Asp
 1               5                  10                  15

TGG GAA AAA GAT GAA CCC CAG TGC TGC TTA GAA GAC CCG GCT GTA AGC    96
Trp Glu Lys Asp Glu Pro Gln Cys Cys Leu Glu Asp Pro Ala Val Ser
                20                  25                  30

CCC CTG GAA CCA GGC CCA AGC CTC CCC GCC ATG AAT TTT GTT CAC ACA   144
Pro Leu Glu Pro Gly Pro Ser Leu Pro Ala Met Asn Phe Val His Thr
            35                  40                  45

AGT CCA AAG GTG AAG AAC TTA AAC CCG AAG AAA TTC AGC ATT CAT GAC   192
Ser Pro Lys Val Lys Asn Leu Asn Pro Lys Lys Phe Ser Ile His Asp
        50                  55                  60

CAG GAT CAC AAA GTA CTG GTC CTG GAC TCT GGG AAT CTC ATA GCA GTT   240
Gln Asp His Lys Val Leu Val Leu Asp Ser Gly Asn Leu Ile Ala Val
 65                 70                  75                  80

CCA GAT AAA AAC TAC ATA CGC CCA GAG ATC TTC TTT GCA TTA GCC TCA   288
Pro Asp Lys Asn Tyr Ile Arg Pro Glu Ile Phe Phe Ala Leu Ala Ser
                85                  90                  95

TCC TTG AGC TCA GCC TCT GCG GAG AAA GGA AGT CCG ATT CTC CTG GGG   336
Ser Leu Ser Ser Ala Ser Ala Glu Lys Gly Ser Pro Ile Leu Leu Gly
            100                 105                 110

GTC TCT AAA GGG GAG TTT TGT CTC TAC TGT GAC AAG GAT AAA GGA CAA   384
Val Ser Lys Gly Glu Phe Cys Leu Tyr Cys Asp Lys Asp Lys Gly Gln
        115                 120                 125

AGT CAT CCA TCC CTT CAG CTG AAG AAG GAG AAA CTG ATG AAG CTG GCT   432
Ser His Pro Ser Leu Gln Leu Lys Lys Glu Lys Leu Met Lys Leu Ala
130                 135                 140

GCC CAA AAG GAA TCA GCA CGC CGG CCC TTC ATC TTT TAT AGG GCT CAG   480
Ala Gln Lys Glu Ser Ala Arg Arg Pro Phe Ile Phe Tyr Arg Ala Gln
145                 150                 155                 160

GTG GGC TCC TGG AAC ATG CTG GAG TCG GCG GCT CAC CCC GGA TGG TTC   528
Val Gly Ser Trp Asn Met Leu Glu Ser Ala Ala His Pro Gly Trp Phe
                165                 170                 175
```

```
ATC TGC ACC TCC TGC AAT TGT AAT GAG CCT GTT GGG GTG ACA GAT AAA      576
Ile Cys Thr Ser Cys Asn Cys Asn Glu Pro Val Gly Val Thr Asp Lys
        180                 185                 190

TTT GAG AAC AGG AAA CAC ATT GAA TTT TCA TTT CAA CCA GTT TGC AAA      624
Phe Glu Asn Arg Lys His Ile Glu Phe Ser Phe Gln Pro Val Cys Lys
        195                 200                 205

GCT GAA ATG AGC CCC AGT GAG GTC AGC GAT TAG                          657
Ala Glu Met Ser Pro Ser Glu Val Ser Asp
        210                 215
```

(2) INFORMATION FOR SEQ ID NO: 4:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ser Phe Val Gly Glu Asn Ser Gly Val Lys Met Gly Ser Glu Asp
 1               5                  10                  15

Trp Glu Lys Asp Glu Pro Gln Cys Cys Leu Glu Asp Pro Ala Val Ser
                20                  25                  30

Pro Leu Glu Pro Gly Pro Ser Leu Pro Ala Met Asn Phe Val His Thr
            35                  40                  45

Ser Pro Lys Val Lys Asn Leu Asn Pro Lys Lys Phe Ser Ile His Asp
        50                  55                  60

Gln Asp His Lys Val Leu Val Leu Asp Ser Gly Asn Leu Ile Ala Val
 65                  70                  75                  80

Pro Asp Lys Asn Tyr Ile Arg Pro Glu Ile Phe Phe Ala Leu Ala Ser
                85                  90                  95

Ser Leu Ser Ser Ala Ser Ala Glu Lys Gly Ser Pro Ile Leu Leu Gly
            100                 105                 110

Val Ser Lys Gly Glu Phe Cys Leu Tyr Cys Asp Lys Asp Lys Gly Gln
        115                 120                 125

Ser His Pro Ser Leu Gln Leu Lys Glu Lys Leu Met Lys Leu Ala
    130                 135                 140

Ala Gln Lys Glu Ser Ala Arg Arg Pro Phe Ile Phe Tyr Arg Ala Gln
145                 150                 155                 160

Val Gly Ser Trp Asn Met Leu Glu Ser Ala Ala His Pro Gly Trp Phe
                165                 170                 175

Ile Cys Thr Ser Cys Asn Cys Asn Glu Pro Val Gly Val Thr Asp Lys
            180                 185                 190

Phe Glu Asn Arg Lys His Ile Glu Phe Ser Phe Gln Pro Val Cys Lys
        195                 200                 205

Ala Glu Met Ser Pro Ser Glu Val Ser Asp
    210                 215
```

(2) INFORMATION FOR SEQ ID NO: 5:

(i) SEQUENCE CHARACTERISTICS:
        (A) LENGTH: 159 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 5:

```
Ser Ala Pro Phe Ser Phe Leu Ser Asn Val Lys Tyr Asn Phe Met Arg
 1               5                  10                  15

Ile Ile Lys Tyr Glu Phe Ile Leu Asn Asp Ala Leu Asn Gln Ser Ile
                20                  25                  30

Ile Arg Ala Asn Asp Gln Tyr Leu Thr Ala Ala Leu His Asn Leu
             35                  40                  45

Asp Glu Ala Val Lys Phe Asp Met Gly Ala Tyr Lys Ser Ser Lys Asp
        50                  55                  60

Asp Ala Lys Ile Thr Val Ile Leu Arg Ile Ser Lys Thr Gln Leu Tyr
 65                 70                  75                  80

Val Thr Ala Gln Asp Glu Asp Gln Pro Val Leu Leu Lys Glu Met Pro
                85                  90                  95

Glu Ile Pro Lys Thr Ile Thr Gly Ser Glu Thr Asn Leu Leu Phe Phe
                100                 105                 110

Trp Glu Thr His Gly Thr Lys Asn Tyr Phe Thr Ser Val Ala His Pro
                115                 120                 125

Asn Leu Phe Ile Ala Thr Lys Gln Asp Tyr Trp Val Cys Leu Ala Gly
                130                 135                 140

Gly Pro Pro Ser Ile Thr Asp Phe Gln Ile Leu Glu Asn Gln Ala
145                 150                 155
```

(2) INFORMATION FOR SEQ ID NO: 6:

(i) SEQUENCE CHARACTERISTICS:
        (A) LENGTH: 156 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 6:

```
Ser Ala Pro Tyr Thr Tyr Gln Ser Asp Leu Arg Tyr Lys Leu Met Lys
 1               5                  10                  15

Leu Val Arg Gln Lys Phe Val Met Asn Asp Ser Leu Asn Gln Thr Ile
                20                  25                  30

Tyr Gln Asp Val Asp Lys His Tyr Leu Ser Thr Thr Trp Leu Asn Asp
             35                  40                  45

Leu Gln Gln Glu Val Lys Phe Asp Met Tyr Ala Tyr Ser Ser Gly Gly
        50                  55                  60

Asp Asp Ser Lys Tyr Pro Val Thr Leu Lys Ile Ser Asp Ser Gln Leu
 65                 70                  75                  80

Phe Val Ser Ala Gln Gly Glu Asp Gln Pro Val Leu Leu Lys Glu Leu
                85                  90                  95

Pro Glu Thr Pro Lys Leu Ile Thr Gly Ser Glu Thr Asp Leu Ile Phe
                100                 105                 110

Phe Trp Lys Ser Ile Asn Ser Lys Asn Tyr Phe Thr Ser Ala Ala Tyr
                115                 120                 125

Pro Glu Leu Phe Ile Ala Thr Lys Glu Gln Ser Arg Val His Leu Ala
                130                 135                 140

Arg Gly Leu Pro Ser Met Thr Asp Phe Gln Ile Ser
145                 150                 155
```

(2) INFORMATION FOR SEQ ID NO: 7:

(i) SEQUENCE CHARACTERISTICS:
        (A) LENGTH: 158 amino acids

```
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 7:

Asp Tyr Phe Gly Lys Leu Glu Ser Lys Leu Ser Val Ile Arg Asn Leu
1               5                   10                  15

Asn Asp Gln Val Leu Phe Ile Asp Gln Gly Asn Arg Pro Leu Phe Glu
            20                  25                  30

Asp Met Thr Asp Ser Asp Cys Arg Asp Asn Ala Pro Arg Thr Ile Phe
        35                  40                  45

Ile Ile Ser Met Tyr Lys Asp Ser Gln Pro Arg Gly Met Ala Val Thr
    50                  55                  60

Ile Ser Val Lys Cys Glu Lys Ile Ser Thr Leu Ser Cys Glu Asn Lys
65              70                  75                  80

Ile Ile Ser Phe Lys Glu Met Asn Pro Pro Asp Asn Ile Lys Asp Thr
            85                  90                  95

Lys Ser Asp Ile Ile Phe Phe Gln Arg Ser Val Pro Gly His Asp Asn
            100                 105                 110

Lys Met Gln Phe Glu Ser Ser Ser Tyr Glu Gly Tyr Phe Leu Ala Cys
            115                 120                 125

Glu Lys Glu Arg Asp Leu Phe Lys Leu Ile Leu Lys Lys Glu Asp Glu
            130                 135                 140

Leu Gly Asp Arg Ser Ile Met Phe Thr Val Gln Asn Glu Asp
145                 150                 155

(2) INFORMATION FOR SEQ ID NO: 8:

(i) SEQUENCE CHARACTERISTICS:
        (A) LENGTH: 158 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 8:

Asp Asn Phe Gly Arg Leu His Cys Thr Thr Ala Val Ile Arg Asn Ile
1               5                   10                  15

Asn Asp Gln Val Leu Phe Val Asp Lys Arg Gln Pro Val Phe Glu Asp
            20                  25                  30

Met Thr Asp Ile Asp Gln Ser Ala Ser Glu Pro Gln Thr Arg Leu Ile
        35                  40                  45

Ile Tyr Met Tyr Lys Asp Ser Glu Val Arg Gly Leu Ala Val Thr Leu
    50                  55                  60

Ser Val Lys Asp Ser Lys Met Ser Thr Leu Ser Cys Lys Asn Lys Ile
65              70                  75                  80

Ile Ser Phe Glu Glu Met Asp Pro Pro Glu Asn Ile Asp Asp Ile Gln
            85                  90                  95

Ser Asp Leu Ile Phe Phe Gln Lys Arg Val Pro Gly His Asn Lys Met
            100                 105                 110

Glu Phe Glu Ser Ser Leu Tyr Glu Gly His Phe Leu Ala Cys Gln Lys
            115                 120                 125

Glu Asp Asp Ala Phe Lys Leu Ile Leu Lys Lys Lys Asp Glu Asn Gly
            130                 135                 140

Asp Lys Ser Val Met Phe Thr Leu Thr Asn Leu His Gln Ser
```

(2) INFORMATION FOR SEQ ID NO: 9:

(i) SEQUENCE CHARACTERISTICS:
        (A) LENGTH: 154 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 9:

```
Asp Ala Pro Val Arg Ser Leu Asn Cys Thr Leu Arg Asp Ser Gln Gln
1               5                  10                  15

Lys Ser Leu Val Met Ser Gly Pro Tyr Glu Leu Lys Ala Leu His Leu
            20                  25                  30

Gln Gly Gln Asp Met Glu Gln Gln Val Val Phe Ser Met Ser Phe Val
        35                  40                  45

Gln Gly Glu Glu Ser Asn Asp Lys Ile Pro Val Ala Leu Gly Leu Lys
    50                  55                  60

Glu Lys Asn Leu Tyr Leu Ser Cys Val Leu Lys Asp Asp Lys Pro Thr
65                  70                  75                  80

Leu Gln Leu Glu Ser Val Asp Pro Lys Asn Tyr Pro Lys Lys Lys Met
                85                  90                  95

Glu Lys Arg Phe Val Phe Asn Lys Ile Glu Ile Asn Asn Lys Leu Glu
            100                 105                 110

Phe Glu Ser Ala Gln Phe Pro Asn Trp Tyr Ile Ser Thr Ser Gln Ala
        115                 120                 125

Glu Asn Met Pro Val Phe Leu Gly Gly Thr Lys Gly Gly Gln Asp Ile
    130                 135                 140

Thr Asp Phe Thr Met Gln Phe Val Ser Ser
145                 150
```

(2) INFORMATION FOR SEQ ID NO: 10:

(i) SEQUENCE CHARACTERISTICS:
        (A) LENGTH: 153 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 10:

```
Asp Val Pro Ile Arg Gln Leu His Tyr Arg Leu Arg Asp Glu Gln Gln
1               5                  10                  15

Lys Ser Leu Val Leu Ser Asp Pro Tyr Glu Leu Lys Ala Leu His Leu
            20                  25                  30

Asn Gly Gln Asn Ile Asn Gln Gln Val Ile Phe Ser Met Ser Phe Val
        35                  40                  45

Gln Gly Glu Pro Ser Asn Asp Lys Ile Pro Val Ala Leu Gly Leu Lys
    50                  55                  60

Gly Lys Asn Leu Tyr Leu Ser Cys Val Met Lys Asp Gly Thr Pro Thr
65                  70                  75                  80

Leu Gln Leu Glu Ser Val Asp Pro Lys Gln Tyr Pro Lys Lys Lys Met
                85                  90                  95

Glu Lys Arg Phe Val Phe Asn Lys Ile Glu Val Lys Ser Lys Val Glu
            100                 105                 110
```

```
Phe Glu Ser Ala Glu Phe Pro Asn Trp Tyr Ile Ser Thr Ser Gln Ala
        115                 120                 125
Glu His Lys Pro Val Phe Leu Gly Asn Asn Ser Gly Gln Asp Ile Ile
        130                 135                 140
Asp Phe Thr Met Glu Ser Val Ser Ser
145                 150

(2) INFORMATION FOR SEQ ID NO: 11:

(i) SEQUENCE CHARACTERISTICS:
          (A) LENGTH: 153 amino acids
          (B) TYPE: amino acid
          (C) STRANDEDNESS: not relevant
          (D) TOPOLOGY: linear (ii) MOLECULE TYPE: peptide (xi) SEQUENCE DESCRIPTION: SEQ ID NO: 11:

Cys Arg Pro Ser Gly Arg Lys Ser Ser Lys Met Gln Ala Phe Arg Ile
1               5                   10                  15
Trp Asp Val Asn Gln Lys Thr Phe Tyr Leu Arg Asn Asn Gln Leu Val
                20                  25                  30
Ala Gly Tyr Leu Gln Gly Pro Asn Val Asn Leu Glu Glu Lys Ile Asp
            35                  40                  45
Val Val Pro Ile Glu Pro His Ala Leu Phe Leu Gly Ile His Gly Gly
        50                  55                  60
Lys Leu Cys Leu Ser Cys Val Lys Ser Gly Asp Glu Thr Arg Leu Gln
65                  70                  75                  80
Leu Glu Ala Val Asn Ile Thr Asp Leu Ser Glu Asn Arg Lys Gln Asp
                85                  90                  95
Lys Arg Phe Ala Phe Ile Arg Ser Asp Ser Gly Pro Thr Thr Ser Phe
            100                 105                 110
Glu Ser Ala Ala Cys Pro Gly Trp Phe Leu Cys Thr Ala Met Glu Ala
        115                 120                 125
Asp Gln Pro Val Ser Leu Thr Asn Met Pro Asp Glu Gly Val Met Val
        130                 135                 140
Thr Lys Phe Tyr Phe Gln Glu Asp Glu
145                 150

(2) INFORMATION FOR SEQ ID NO: 12:

(i) SEQUENCE CHARACTERISTICS:
          (A) LENGTH: 153 amino acids
          (B) TYPE: amino acid
          (C) STRANDEDNESS: not relevant
          (D) TOPOLOGY: linear (ii) MOLECULE TYPE: peptide (xi) SEQUENCE DESCRIPTION: SEQ ID NO: 12:

Cys Arg Pro Ser Gly Lys Arg Pro Cys Lys Met Gln Ala Phe Arg Ile
1               5                   10                  15
Trp Asp Thr Asn Gln Lys Thr Phe Tyr Leu Arg Asn Asn Gln Leu Ile
                20                  25                  30
Ala Gly Tyr Leu Gln Gly Pro Asn Ile Lys Leu Glu Glu Lys Ile Asp
            35                  40                  45
Met Val Pro Ile Asp Leu His Ser Val Phe Leu Gly Ile Lys Gly Tyr
        50                  55                  60
Lys Leu Tyr Met Ser Cys Val Lys Ser Gly Asp Asp Ile Lys Leu Gln
65                  70                  75                  80
```

```
Leu Glu Glu Val Asn Ile Thr Asp Leu Ser Lys Asn Lys Glu Asp
                85                  90                  95

Lys Arg Phe Thr Phe Ile Arg Ser Glu Lys Gly Pro Thr Thr Ser Phe
                100                 105                 110

Glu Ser Ala Ala Cys Pro Gly Trp Phe Leu Cys Thr Thr Leu Glu Ala
                115                 120                 125

Asp Arg Pro Val Ser Leu Thr Asn Thr Pro Glu Pro Leu Ile Val
            130                 135                 140

Thr Lys Phe Tyr Phe Gln Glu Asp Gln
145                 150
```

(2) INFORMATION FOR SEQ ID NO: 13:

(i) SEQUENCE CHARACTERISTICS:
        (A) LENGTH: 156 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 13:

```
Met Met Val Leu Ser Gly Ala Leu Cys Phe Arg Met Lys Asp Ser Ala
1               5                   10                  15

Leu Lys Val Leu Tyr Leu His Asn Asn Gln Leu Leu Ala Gly Gly Leu
                20                  25                  30

His Ala Glu Lys Val Ile Lys Gly Glu Glu Ile Ser Val Val Pro Asn
            35                  40                  45

Arg Ala Leu Asp Ala Ser Leu Ser Pro Val Ile Leu Gly Val Gln Gly
        50                  55                  60

Gly Ser Gln Cys Leu Ser Cys Gly Thr Glu Lys Gly Pro Ile Leu Lys
65                  70                  75                  80

Leu Glu Pro Val Asn Ile Met Glu Leu Tyr Leu Gly Ala Lys Glu Ser
                85                  90                  95

Lys Ser Phe Thr Phe Tyr Arg Arg Asp Met Gly Leu Thr Ser Ser Phe
                100                 105                 110

Glu Ser Ala Ala Tyr Pro Gly Trp Phe Leu Cys Thr Ser Pro Glu Ala
                115                 120                 125

Asp Gln Pro Val Arg Leu Thr Gln Ile Pro Glu Asp Pro Ala Trp Asp
            130                 135                 140

Ala Pro Ile Thr Asp Phe Tyr Phe Gln Gln Cys Asp
145                 150                 155
```

(2) INFORMATION FOR SEQ ID NO: 14:

(i) SEQUENCE CHARACTERISTICS:
        (A) LENGTH: 160 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 14:

```
Met Asn Lys Glu Lys Glu Leu Arg Ala Ala Ser Pro Ser Leu Arg His
1               5                   10                  15

Val Gln Asp Leu Ser Ser Arg Val Trp Ile Leu Gln Asn Asn Ile Leu
                20                  25                  30

Thr Ala Val Pro Arg Lys Glu Gln Thr Val Pro Val Thr Ile Thr Leu
```

-continued

```
                35                  40                  45
Leu Pro Cys Gln Tyr Leu Asp Thr Leu Glu Thr Asn Arg Gly Asp Pro
 50                  55                  60

Thr Tyr Met Gly Val Gln Arg Pro Met Ser Cys Leu Phe Cys Thr Lys
 65                  70                  75                  80

Asp Gly Glu Gln Pro Val Leu Gln Leu Gly Glu Gly Asn Ile Met Glu
                 85                  90                  95

Met Tyr Asn Lys Lys Glu Pro Val Lys Ala Ser Leu Phe Tyr His Lys
                100                 105                 110

Lys Ser Gly Thr Thr Ser Thr Phe Glu Ser Ala Ala Phe Pro Gly Trp
                115                 120                 125

Phe Ile Ala Val Cys Ser Lys Gly Ser Cys Pro Leu Ile Leu Thr Gln
                130                 135                 140

Glu Leu Gly Glu Ile Phe Ile Thr Asp Phe Glu Met Ile Val Val His
145                 150                 155                 160
```

(2) INFORMATION FOR SEQ ID NO: 15:

(i) SEQUENCE CHARACTERISTICS:
        (A) LENGTH: 169 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 15:

```
Met Arg Gly Thr Pro Gly Asp Ala Asp Gly Gly Arg Ala Val Tyr
 1               5                  10                  15

Gln Ser Met Cys Lys Pro Ile Thr Gly Thr Ile Asn Asp Leu Asn Gln
                 20                  25                  30

Gln Val Trp Thr Leu Gln Gly Gln Asn Leu Val Ala Val Pro Arg Ser
                 35                  40                  45

Asp Ser Val Thr Pro Val Thr Val Ala Val Ile Thr Cys Lys Tyr Pro
 50                  55                  60

Glu Ala Leu Glu Gln Gly Arg Gly Asp Pro Ile Tyr Leu Gly Ile Gln
 65                  70                  75                  80

Asn Pro Glu Met Cys Leu Tyr Cys Glu Lys Val Gly Glu Gln Pro Thr
                 85                  90                  95

Leu Gln Leu Lys Glu Gln Lys Ile Met Asp Leu Tyr Gly Gln Pro Glu
                100                 105                 110

Pro Val Lys Pro Phe Leu Phe Tyr Arg Ala Lys Thr Gly Arg Thr Ser
                115                 120                 125

Thr Leu Glu Ser Val Ala Phe Pro Asp Trp Phe Ile Ala Ser Ser Lys
                130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                165
```

IL-1-LIKE CYTOKINE ANTIBODIES

This filing is a divisional of commonly assigned, U.S. patent application Ser. No. 10/695,195, filed Oct. 27, 2003, now U.S. Pat. No. 7,108,850, which is a divisional of commonly assigned, U.S. patent application Ser. No. 09/398,412, filed Sep. 17, 1999, now U.S. Pat. No. 6,680,380, which claims benefit of U.S. Provisional Patent Application U.S. Ser. No. 60/100,948, filed Sep. 18, 1998, each of which is incorporated by reference.

FIELD OF THE INVENTION

The present invention relates to compositions and methods for affecting mammalian physiology, including morphogenesis or immune system function. In particular, it provides nucleic acids, proteins, and antibodies which regulate development and/or the immune system. Diagnostic and therapeutic uses of these materials are also disclosed.

BACKGROUND OF THE INVENTION

Recombinant DNA technology refers generally to techniques of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the immune response does, in fact, revolve around the network-like interactions of lymphocytes, macrophages, granulocytes, and other cells, immunologists now generally hold the opinion that soluble proteins, known as lymphokines, cytokines, or monokines, play critical roles in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. They have been shown to support the proliferation, growth, and/or differentiation of pluripotent hematopoietic stem cells into vast numbers of progenitors comprising diverse cellular lineages which make up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

Research to better understand and treat various immune disorders has been hampered by the general inability to maintain cells of the immune system in vitro. Immunologists have discovered that culturing many of these cells can be accomplished through the use of T-cell and other cell supernatants, which contain various growth factors, including many of the lymphokines.

The interleukin-1 family of proteins includes the IL-1α, the IL-1β, the IL-1RA, and recently the IL-1γ (also designated Interferon-Gamma Inducing Factor, IGIF). This related family of genes has been implicated in a broad range of biological functions. See Dinarello (1994) *FASEB J.* 8:1314-1325; Dinarello (1991) *Blood* 77:1627-1652; and Okamura, et al. (1995) *Nature* 378:88-91.

In addition, various growth and regulatory factors exist which modulate morphogenetic development. This includes, e.g., the Toll ligands, which signal through binding to receptors which share structural, and mechanistic, features characteristic of the IL-1 receptors. See, e.g., Lemaitre, et al. (1996) *Cell* 86:973-983; and Belvin and Anderson (1996) *Ann. Rev. Cell & Develop. Biol.* 12:393-416.

From the foregoing, it is evident that the discovery and development of new soluble proteins, including ones similar to lymphokines, should contribute to new therapies for a wide range of degenerative or abnormal conditions which directly or indirectly involve development, differentiation, or function, e.g., of the immune system and/or hematopoietic cells. In particular, the discovery and understanding of novel lymphokine-like molecules which enhance or potentiate the beneficial activities of other lymphokines would be highly advantageous. The present invention provides new interleukin-1 like compositions and related compounds, and methods for their use.

SUMMARY OF THE INVENTION

The present invention is based on the discovery, purification, and characterization of the biological activities of a novel mammalian, e.g., primate, interleukin-1 like molecule, designated interleukin-1ζ (IL-1ζ). IL-1ζ exhibits both structural and sequence similarity, e.g., by homology comparison, to known members of the IL-1 family of molecules.

In a first aspect, the invention provides an isolated or recombinant polypeptide that: specifically binds polyclonal antibodies generated against at least a 12 consecutive amino acid segment of SEQ ID NO: 2 or 4; and comprises at least one sequence selected from: GENSGVK; EDWEKD; CCLEDPA; FVHTSR; KKFSIHD; VLVLDS; NLIAVP; FFALAS; SSASAEK; SLILLGV; FCLYCDK; PSLQLK; KLMKLAAQ; FIFYRAQ; SRNMLES; WFICTS; EPVGVT; or FSFQPVC (see SEQ ID NO: 2); or FVHTSP; SPILLGV; or SWNMLES (see SEQ ID NO: 4). Certain embodiments include those: wherein the polypeptide comprises a plurality of the sequence; or which specifically bind to polyclonal antibodies generated against an immunogen selected from SEQ ID NO: 2 or 4. Other embodiments include those where the 12 consecutive amino acid segment is selected from: GVKMGSEDWEKD; AGSPLEPGPSLP; SRKVKSLNPKKF; HDQDHKVLVLDS; NLIAVPDKNYIR; FALASSLSSASA; GQSHPSLQLKKE; MKLAAQKESARR; FYRAQVGSRNML; TSCNCNEPVGVT; FENRKHIEFSFQ; or PVCKAEMSPSEV (see SEQ ID NO: 2); or AVSPLEPGPSLP; SPKVKNLNPKKF; or FYRAQVGSWNML (see SEQ ID NO: 4). Certain preferred embodiments include those wherein the polypeptide: comprises a mature protein; lacks a post-translational modification; is from a primate, including a human; is a natural allelic variant of IL-1ζ; has a length at least about 30 amino acids; exhibits at least two non-overlapping epitopes that are specific for a primate IL-1ζ; exhibits a sequence identity over a length of at least about 20 amino acids to SEQ ID NO: 2 or 4; is not glycosylated; has a molecular weight of at least 10 kD with natural glycosylation; is a synthetic polypeptide; is attached to a solid substrate; is conjugated to another chemical moiety; is a 5-fold or less substitution from natural sequence; or is a deletion or insertion variant from a natural sequence.

Other embodiments include a soluble polypeptide comprising: the sterile polypeptide; the sterile polypeptide and a carrier, wherein the carrier is: an aqueous compound, including water, saline, and/or buffer; and/or formulated for oral, rectal, nasal, topical, or parenteral administration.

Fusion protein embodiments include those having a polypeptide sequence described, further comprising: a mature polypeptide as described; a detection or purification tag, including a FLAG, His6, or Ig sequence; or sequence of another cytokine or chemokine.

Kit embodiments include those comprising such a polypeptide and: a compartment comprising said polypeptide; and/or instructions for use or disposal of reagents in said kit.

Antibody or binding compound embodiments encompass a binding compound comprising an antigen binding site from an antibody, which specifically binds to a mature polypeptide, as described, wherein: the mature polypeptide is a primate IL-1ζ; the binding compound is an Fv, Fab, or Fab2 fragment; the binding compound is conjugated to another chemical moiety; or the antibody: is raised against a 12 consecutive amino acid segment of SEQ ID NO: 2 or 4; is raised against a mature IL-1ζ; is raised to a purified primate IL-1ζ; is immunoselected; is a polyclonal antibody; binds to a denatured IL-1ζ; exhibits a Kd to antigen of at least 30 µM; is attached to a solid substrate, including a bead or plastic membrane; is in a sterile composition; or is detectably labeled, including a radioactive or fluorescent label. An alternative binding compound embraces one comprising an antigen binding portion from an antibody, which specifically binds to a primate protein, as described, wherein: the protein is a human protein; the binding compound is an Fv, Fab, or Fab2 fragment; the binding compound is conjugated to another chemical moiety; or the antibody: is raised against a polypeptide sequence of a mature polypeptide comprising at least 12 consecutive amino acids of SEQ ID NO: 2 or 4; is raised against a mature primate IL-1ζ; is raised to a purified primate IL-1ζ; is immunoselected; is a polyclonal antibody; binds to a denatured primate IL-1ζ; exhibits a Kd to antigen of at least 30 µM; is attached to a solid substrate, including a bead or plastic membrane; is in a sterile composition; or is detectably labeled, including a radioactive or fluorescent label. Kits are provided comprising the binding compound, as described, and: a compartment comprising said binding compound; and/or instructions for use or disposal of reagents in the kit. Methods are also provided, e.g., of: making an antibody, comprising immunizing an immune system with an immunogenic amount of: a primate IL-1ζ polypeptide; or a peptide sequence comprising at least 12 consecutive amino acids of SEQ ID NO: 2 or 4; thereby causing said antibody to be produced; or producing an antigen:antibody complex, comprising contacting a primate IL-1ζ polypeptide with an antibody, as described, thereby allowing said complex to form.

The invention further embraces a composition comprising: the sterile binding compound described, or the binding compound and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding the described polypeptide, wherein: the polypeptide is a primate IL-1ζ; or the nucleic acid: encodes an antigenic peptide sequence of SEQ ID NO: 2 or 4; encodes a plurality of antigenic peptide sequences of SEQ ID NO: 2 or 4; exhibits at least about 80% identity to a natural cDNA encoding said segment; is an expression vector; further comprises an origin of replication; is from a natural source; comprises a detectable label; comprises synthetic nucleotide sequence; is less than 6 kb, preferably less than 3 kb; is from a rodent; comprises a natural full length coding sequence; is a hybridization probe for a gene encoding said IL-1ζ; or is a PCR primer, PCR product, or mutagenesis primer; or encodes an IL-1ζ polypeptide. The invention also provides a cell transformed with the described nucleic acid, e.g., where the cell is: a prokaryotic cell; a eukaryotic cell; a bacterial cell; a yeast cell; an insect cell; a mammalian cell; a mouse cell; a primate cell; or a human cell.

Another embodiment is a kit comprising the described nucleic acid and: a compartment comprising said nucleic acid and: a compartment further comprising a primate IL-1ζ polypeptide; and/or instructions for use or disposal of reagents in said kit.

Other nucleic acid embodiments include an isolated or recombinant nucleic acid that hybridizes under wash conditions of 30° C. and less than 2M salt to SEQ ID NO: 1; or where the wash condition is at: 45° C. and/or 500 mM salt; 55° C. and/or 150 mM salt; or encodes at least 12 or 17 contiguous amino acids of SEQ ID NO: 2 or 4.

The invention also provides methods of modulating a cell involved in an inflammatory response comprising contacting said cell with an agonist or antagonist of a primate IL-1ζ polypeptide. Preferably, the contacting is in combination with an agonist or antagonist of IL-1α, IL-1RA, IL-1β, IL-1γ, IL-1δ, IL-1ε, IL-2, and/or IL-12; the contacting is with an antagonist, including binding composition comprising an antibody binding site which specifically binds an IL-1ζ; or the modulating is regulation of IFN-γ production.

DETAILED DESCRIPTION OF THE PREFERRED EMBODIMENTS

Outline

I. General

II. Activities

III. Nucleic Acids
   A. encoding fragments, sequence, probes
   B. mutations, chimeras, fusions
   C. making nucleic acids
   D. vectors, cells comprising IV. Proteins, Peptides
   A. fragments, sequence, immunogens, antigens
   B. muteins
   C. agonists/antagonists, functional equivalents
   D. making proteins V. Making Nucleic Acids, Proteins VI. Antibodies
   A. polyclonals
   B. monoclonal, Kd
   C. anti-idiotypic antibodies
   D. hybridoma cell lines VII. Kits and Methods to Quantify IL-1ζ
   A. ELISA
   B. assay mRNA encoding
   C. qualitative/quantitative
   D. kits VIII. Therapeutic Compositions, Methods
   A. combination compositions
   B. unit dose
   C. administration IX. Receptors I. General Before the present compositions, formulations, and methods are described, it is to be understood that this invention is not limited to the particular methods, compositions, and cell lines described herein, as such methods, compositions, and cell lines may, of course, vary. It is also to be understood that the terminology used herein is for the purpose of describing particular embodiments only, and is not intended to limit the scope of the present invention which is only defined by the appended claims.

As used herein, including the appended claims, singular forms of words such as "a," "an," and "the" include their corresponding plural referents unless the context clearly dictates otherwise. Thus, e.g., reference to "an organism" includes one or more different organisms, reference to "a cell" includes one or more of such cells, and reference to "a method" includes reference to equivalent steps and methods known to a person of ordinary skill in the art, and so forth.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patents, and other references discussed above are provided solely for their disclosure prior to the filing date of the present application. Nothing herein is to be construed as an admission that the invention is not entitled to antedate such disclosure by virtue of its prior invention. All publications, patent applications, patents, and other references mentioned herein are incorporated by reference in their entirety including all figures and drawings.

The present invention provides the amino acid sequence and DNA sequence of a mammalian, e.g., human, interleukin-1 like molecule having particular defined properties, both structural and biological. This has been designated herein as interleukin-1ζ, and increases the number of members of the IL-1 family from 6 to 7. Various cDNAs encoding these molecules were obtained from primate, e.g., human, cDNA sequence libraries. Rodent counterparts should also exist. The nucleic acids encompassed herein include DNA, cDNA, and RNA sequences which encode IL-1ζ. It is understood that nucleic acids encoding all or a portion of IL-1ζ polypeptides are also encompassed, so long as they encode a polypeptide with IL-1ζ activity. Such nucleic acids include both naturally occurring and intentionally manipulated nucleic acids. For example, IL-1ζ may be subjected to site-directed mutagenesis.

Some of the standard methods applicable are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1-3, CSH Press, NY; Ausubel, et al., *Biology*, Greene Publishing Associates, Brooklyn, N.Y.; or Ausubel, et al. (1987 and periodic supplements) *Current Protocols in Molecular Biology*, Greene/Wiley, New York; each of which is incorporated herein by reference.

A complete nucleotide (SEQ ID NO: 1) and corresponding amino acid sequence (SEQ ID NO: 2) of a primate IL-1ζ coding segment is shown in Table 1. An alternative sequence, perhaps an allelic variant, is presented as SEQ ID NO: 3 and 4. Table 2 provides an alignment of selected family members.

TABLE 1

Nucleotide and amino acid sequences (see SEQ ID NO: 1-4) of mammalian, e.g., primate, IL-1ζ.

| | | | | | |
|---|---|---|---|---|---|
| CGGTTTGTTT | TCTTTAGAGA | TTTTACAGTG | TTGGTTATAA | TTGTGCACTT AATCTTTATT | 60 |
| TTCCTTATAC | AGTAGTCCCC | CCGATCAACT | GGGGGCATGT | TCCATACCCC TGGTGGATTC | 120 |
| CTGAAACTGC | CAGTTAGTAC | CAAACCCTAT | ATAGATTGTG | TTTTTTCCTG TACGCAGGCC | 180 |
| GACACACAGG | AAATCATAAG | TCAGGAGGGC | CACTGCCACG | CAGGAAAGAC CCATCTGAAC | 240 |
| TGCTGCAAAA | GCTCCGTGTC | GATTTATTGC | TTCCACAAAT | AGTGCCGATA TGCACCAGGC | 300 |
| ACTGTTGTAA | AACTGAAAAT | ATGTTTTGGG | ATGTGCCCAG | TCTACCTAGC TCCTTCAAGT | 360 |
| AAAGGATCCT | GAGAACTGAA | GGCAAACAGA | GCTCCAGGAG | TCCAAGACAG AGCCACACAC | 420 |
| CACGAGGATC | CTGGCCCAGG | TCTTGGACTT | CCATTCCCAT | TTCTGTTGAG TAATAAACTC | 480 |

AACGTTGAAA ATG TCC TTT GTG GGG GAG AAC TCA GGA GTG AAA ATG GGC     529
               Met Ser Phe Val Gly Glu Asn Ser Gly Val Lys Met Gly
               1            5            10

TABLE 1-continued

Nucleotide and amino acid sequences (see SEQ ID NO: 1-4) of mammalian, e.g., primate, IL-1ζ.

```
TCT GAG GAC TGG GAA AAA GAT GAA CCC CAG TGC TGC TTA GAA GAC CCG    577
Ser Glu Asp Trp Glu Lys Asp Glu Pro Gln Cys Cys Leu Glu Asp Pro
     15                  20                  25

GCT GGA AGC CCC CTG GAA CCA GGC CCA AGC CTC CCC ACC ATG AAT TTT    625
Ala Gly Ser Pro Leu Glu Pro Gly Pro Ser Leu Pro Thr Met Asn Phe
 30              35                  40                  45

GTT CAC ACA AGT CGA AAG GTG AAG AGC TTA AAC CCG AAG AAA TTC AGC    673
Val His Thr Ser Arg Lys Val Lys Ser Leu Asn Pro Lys Lys Phe Ser
                 50                  55                  60

ATT CAT GAC CAG GAT CAC AAA GTA CTG GTC CTG GAC TCT GGG AAT CTC    721
Ile His Asp Gln Asp His Lys Val Leu Val Leu Asp Ser Gly Asn Leu
                 65                  70                  75

ATA GCA GTT CCA GAT AAA AAC TAC ATA CGC CCA GAG ATC TTC TTT GCA    769
Ile Ala Val Pro Asp Lys Asn Tyr Ile Arg Pro Glu Ile Phe Phe Ala
             80                  85                  90

TTA GCC TCA TCC TTG AGC TCA GCC TCT GCG GAG AAA GGA AGT CTG ATT    817
Leu Ala Ser Ser Leu Ser Ser Ala Ser Ala Glu Lys Gly Ser Leu Ile
         95                 100                 105

CTC CTG GGG GTC TCT AAA GGG GAG TTT TGT CTC TAC TGT GAC AAG GAT    865
Leu Leu Gly Val Ser Lys Gly Glu Phe Cys Leu Tyr Cys Asp Lys Asp
110                 115                 120                 125

AAA GGA CAA AGT CAT CCA TCC CTT CAG CTG AAG AAG GAG AAA CTG ATG    913
Lys Gly Gln Ser His Pro Ser Leu Gln Leu Lys Lys Glu Lys Leu Met
                    130                 135                 140

AAG CTG GGT GCG CAA AAG GAA TCA GCA CGC CGG CCC TTC ATC TTT TAT    961
Lys Leu Ala Ala Gln Lys Glu Ser Ala Arg Arg Pro Phe Ile Phe Tyr
            145                 150                 155

AGG GCT GAG GTG GGG TCC GGG AAC ATG CTG GAG TCG GGG GCT GAG CCC    1009
Arg Ala Glu Val Gly Ser Arg Asn Met Leu Glu Ser Ala Ala His Pro
                160                 165                 170

GGA TGG TTC ATC TGC ACC TCC TGC AAT TGT AAT GAG CCT GTT GGG GTG    1057
Gly Trp Phe Ile Cys Thr Ser Cys Asn Cys Asn Glu Pro Val Gly Val
        175                 180                 185

ACA GAT AAA TTT GAG AAC AGG AAA CAC ATT GAA TTT TCA TTT CAA GGA    1105
Thr Asp Lys Phe Glu Asn Arg Lys His Ile Glu Phe Ser Phe Gln Pro
190                 195                 200                 205

GTT TGC AAA GCT GAA ATG AGC CCC AGT GAG GTC AGC GAT TAGGAAACTG     1154
Val Cys Lys Ala Glu Met Ser Pro Ser Glu Val Ser Asp
                    210                 215

CCCCATTGAA CGCCTTCCTC GCTAATTTGA ACTAATTGTA TAAAAACCCC AAACCTGCTC  1214

ACTAAAAAAA A                                                       1225
```

MSFVGENSGVKMGSEDWEKDEPQCCLEDPAGSPLEPGPSLPTMNFVHTSRKVKSLNPKKFSIHDQDHKV
LVLDSGNLIAVPDKNYIRPEIFFALASSLSSASAEKGSLILLGVSKGEFCLYCDKDKGQSHPSLQLKKE
KLMKLAAQKESARRPFIFYRAQVGSRNMLESAAHPGWFICTSCNCNEPVGVTDKFENRKHIEFSFQPVC
KAEMSPSEVSD

Sequence of a second variant form, which exhibits nucleotide base
changes at nucleotide positions of the coding region: 92 (G->T;
changing amino acids G->V); 124 (A->G; changing T->A); 149 (G->C;
changing R->P); 161 (G->A; changing S->N); 323 (T->G; changing L->P);
and 490 (G->T; changing R->W).

```
ATG TCC TTT GTG GGG GAG AAC TCA GGA GTG AAA ATG GGC TCT GAG GAC    48
Met Ser Phe Val Gly Glu Asn Ser Gly Val Lys Met Gly Ser Glu Asp
  1               5                  10                  15

TGG GAA AAA GAT GAA CCC CAG TGC TGC TTA GAA GAC CCG GCT GTA AGC    96
Trp Glu Lys Asp Glu Pro Gln Cys Cys Leu Glu Asp Pro Ala Val Ser
             20                  25                  30
```

TABLE 1-continued

Nucleotide and amino acid sequences (see SEQ ID NO: 1-4)
of mammalian, e.g., primate, IL-1ζ.

```
CCC CTG GAA CCA GGC CCA AGC CTC CCC GCC ATG AAT TTT GTT CAC ACA    144
Pro Leu Glu Pro Gly Pro Ser Leu Pro Ala Met Asn Phe Val His Thr
        35                  40                  45

AGT GGA AAG GTG AAG AAG TTA AAC CCG AAG AAA TTG AGC ATT CAT GAG    192
Ser Pro Lys Val Lys Asn Leu Asn Pro Lys Lys Phe Ser Ile His Asp
    50                  55                  60

CAG GAT CAC AAA GTA CTG GTC CTG GAC TCT GGG AAT CTC ATA GCA GTT    240
Gln Asp His Lys Val Leu Val Leu Asp Ser Gly Asn Leu Ile Ala Val
65                  70                  75                  80

CCA GAT AAA AAC TAC ATA CGC CCA GAG ATC TTC TTT GCA TTA GCC TCA    288
Pro Asp Lys Asn Tyr Ile Arg Pro Glu Ile Phe Phe Ala Leu Ala Ser
                85                  90                  95

TCC TTG AGC TCA GCC TCT GCG GAG AAA GGA AGT CCG ATT CTC CTG GGG    336
Ser Leu Ser Ser Ala Ser Ala Glu Lys Gly Ser Pro Ile Leu Leu Gly
            100                 105                 110

GTC TCT AAA GGG GAG TTT TGT CTC TAC TGT GAC AAG GAT AAA GGA CAA    384
Val Ser Lys Gly Glu Phe Cys Leu Tyr Cys Asp Lys Asp Lys Gly Gln
        115                 120                 125

AGT CAT CCA TCC CTT GAG CTG AAG AAG GAG AAA CTG ATG AAG CTG GCT    432
Ser His Pro Ser Leu Glu Leu Lys Lys Glu Lys Leu Met Lys Leu Ala
    130                 135                 140

GCC CAA AAG GAA TCA GCA CGC CGG CCC TTC ATC TTT TAT AGG GCT GAG    480
Ala Gln Lys Glu Ser Ala Arg Arg Pro Phe Ile Phe Tyr Arg Ala Glu
145                 150                 155                 160

GTG GGG TCC TGG AAC ATG CTG GAG TCG GCG GCT CAC CCC GGA TGG TTC    528
Val Gly Ser Trp Asn Met Leu Glu Ser Ala Ala His Pro Gly Trp Phe
                165                 170                 175

ATC TGC ACC TCC TGC AAT TGT AAT GAG CCT GTT GGG GTG ACA GAT AAA    576
Ile Cys Thr Ser Cys Asn Cys Asn Glu Pro Val Gly Val Thr Asp Lys
            180                 185                 190

TTT GAG AAC AGG AAA CAC ATT GAA TTT TCA TTT CAA CCA GTT TGC AAA    624
Phe Glu Asn Arg Lys His Ile Glu Phe Ser Phe Gln Pro Val Cys Lys
        195                 200                 205

GCT GAA ATG AGC CCC AGT GAG GTC AGG GAT TAG                        657
Ala Glu Met Ser Pro Ser Glu Val Arg Asp
    210                 215
```

MSFVGENSGVKMGSEDWEKDEPQCCLEDPAVSPLEPGPSLPAMNFVHTSPKVKNLNPKKFSIHDQDHKVL
VLDSGNLIAVPDKNYIRPEIFFALASSLSSASAEKGSPILLGVSKGEFCLYCDKDKGQSHPSLQLKKEKL
MKLAAQKESARRPFIFYRAQVGSWNMLESAAHPGWFICTSCNCNEPVGVTDKFENRKHIEFSFQPVCKAE
MSPSEVSD

The coding sequence does not indicate a signal sequence, which has been reported for various forms of messages encoding other members of the IL-1 family. It is likely that another form of the message probably encodes a signal sequence, much like the IL-1β prodomain which is cleaved by a convertase-like enzyme, see Dinarello (1994) FASEB J. 1314-1325)

TABLE 2

```
IL-1a_human . . . . . . . . . . . . . . . . . . . . . . . . . . . . . . . . . . . . . .SA PFSFLSNVKY
IL-1a_mouse . . . . . . . . . . . . . . . . . . . . . . . . . . . . . . . . . . . . . .SA PYTYQSDLRY
IL-1g_human . . . . . . . . . . . . . . . . . . . . . . . . . . . . . . . . . . . . . . . . . . . . . .
IL-1g_mouse . . . . . . . . . . . . . . . . . . . . . . . . . . . . . . . . . . . . . . . . . . . . . .
IL-1b_human . . . . . . . . . . . . . . . . . . . . . . . . . . . . . . . . . . . . . . . . . . . . . .
IL-1b_mouse . . . . . . . . . . . . . . . . . . . . . . . . . . . . . . . . . . . . . . . . . . . . . .
IL-1x_human . . . . . . . . . . . . . . . . . . . . . . . . . . . . . . . . . . . . . . . . . .CRPS
IL-1x_mouse . . . . . . . . . . . . . . . . . . . . . . . . . . . . . . . . . . . . . . . . . .CRPS
IL-1d_mouse . . . . . . . . . . . . . . . . . . . . . . . . . . . . . . . . . . . . . . . . . . . . . .
IL-1z_human MSFVGENSCV KMGSEDWEKD EPQCCLEDPA GSPLEPGPSL PTMNFVHTSR
IL-1e_mouse . . . . . . . . . . . . . . . . . . . . . . . . . . . . . . . . . . . . . . . .MNKEK
```

TABLE 2-continued

```
IL-1e_human  ........  ........  ........  ....MRGTP  GDADGGGRAV

IL-1a_human  NFMRIIKYEF  ILNDALN...  QSIIRAND..  QYLTAAALHN  LD...EAVKF
IL-1a_mouse  KLMKLVRQKF  VMNDSLN...  QTIYQDVD.K  HYLSTTWLND  LQ...QEVKF
IL-1g_human  ..DYFGKLES  KLSVIRNLND  QVLFIDQGNR  PLFEDMTDSD  CRDNAPRTIF
IL-1g_mouse  ..DNFGRLHC  TTAVIRNIND  QVLFVDKR.Q  PVFEDMTDID  QSASEPQTRL
IL-1b_human  .DAPVRSLNC  TLRDSQQ...  KSLVMSGP..  YELKALHLQG  QDM.EQQVVF
IL-1b_mouse  .DVPIRQLHY  RLRDEQQ...  KSLVLSDP..  YELKALHLNG  QNI.NQQVIF
IL-1x_human  GRKSSKMQAF  RIWDVNQ...  KTFYLRN...  NQLVAGYLQG  PNV.NLEEKI
IL-1x_mouse  GKRPCKMQAF  RIWDTNQ...  KTFYLRN...  NQLIAGYLQG  PNI.KLEEKI
IL-1d_mouse  MMVLSGALCF  PMKDSAL...  KVLYLHN...  NQLLAGGLHA  EKVIKGEEIS
IL-1z_human  KVKSLNPKKF  SIHDQDH...  KVLVLDS...  GNLIAVPDKN  YIR..PEIFF
IL-1e_mouse  ELRAASPSLR  HVQDLSS...  RVWILQN...  NILTAVPRKE  QTV..PVTIT
IL-1e_human  YQSMCKPITG  TINDLNQ...  QVWTLQG...  QNLVAVPRSD  SVT..PVTVA IL-1a_human  DMGAYKSSK.  .DDAKITVIL  RISK.TQLYV  TAQD....ED  QPVLLKEMPE
IL-1a_mouse  DMYAYSSGG.  .DDSKYPVTL  KISD.SQLFV  SAQG....ED  QPVLLKEMPE
IL-1g_human  IISMYKDS..  .QPRGMAVTI  SVKCEKISTL  SCEN......  KIISFKEMNP
IL-1g_mouse  IIYMYKDS..  .EVRGLAVTL  SVKDSKMSTL  SCKN......  KIISFEEMDP
IL-1b_human  SMSFVQGEE.  .SNDKIPVAL  GLKE.KNLYL  SCVL.KD.DK  PTLQLESVDP
IL-1b_mouse  SMSFVQGEP.  .SNDKIPVAL  GLKG.KNLYL  SCVM.KD.GT  PTLQLESVDP
IL-1x_human  DVVPIEP...  .....HALFL  GIHG.GKLCL  SCVK.SG.DE  TRLQLEAVNI
IL-1x_mouse  DMVPIDL...  .....HSVFL  GIKG.YKLYM  SCVK.SG.DD  IKLQLEEVNI
IL-1d_mouse  VVPNRALD..  ..ASLSPVIL  GVQG.GSQCL  SCGT..E.KG  PILKLEPVNI
IL-1z_human  ALASSLSSAS  .AEKGSLILL  GVSK.GEFCL  YCDKDKGQSH  PSLQLKKEKL
IL-1e_mouse  LLPCQYLDTL  ETNRGDPTYM  GVQR.PMSCL  FCTK..DGEQ  PVLQLGEGNI
IL-1e_human  VITCKYPEAL  EQGRGDPIYL  GIQN.PEMCL  YCEK..VGEQ  PTLQLKEQKI IL-1a_human  IPKTITG..S  ETNLLFFWET  HG...TKNYF  TSVAHPNLFI  ATKQ...DYW
IL-1a_mouse  TPKLITG..S  ETDLIFFWKS  IN...SKNYF  TSAAYPELFI  ATKE...QSR
IL-1g_human  PDNIKD...T  KSDIIFFQRS  VPGHDNKMQF  ESSSYEGYFL  ACEKERDLFK
IL-1g_mouse  PENIDD...I  QSDLIFFQKR  VPGH.NKMEF  ESSLYEGHFL  ACQKEDDAFK
IL-1b_human  KNYPKK..KM  EKRFVFNKIE  IN...NKLEF  ESAQFPNWYI  STSQA.ENMP
IL-1b_mouse  KQYPKK..KM  EKRFVFNKIE  VK...SKVEF  ESAEFPNWYI  STSQA.EHKP
IL-1x_human  TDLSENR.KQ  DKRFAFIRSD  SG...PTTSF  ESAACPGWFL  CTAME.ADQP
IL-1x_mouse  TDLSKNK.EE  DKRFTFIRSE  KG...PTTSF  ESAACPGWFL  CTTLE.ADRP
IL-1d_mouse  MELYLGA.KE  SKSFTFYRRD  MG...LTSSF  ESAAYPGWFL  CTSPE.ADQP
IL-1z_human  MKLAAQKESA  RRPFIFYRAQ  .....SRNML  ESAAHPGWFI  CTSCN.CNEP
IL-1e_mouse  MEMYNKK.EP  VKASLFYHKK  SG...TTSTF  ESAAFPGWFI  AVCSK.GSCP
IL-1e_human  MDLYGQP.EP  VKPFLFYRAK  TG...RTSTL  ESVAFPDWFI  ASSKR..DQP IL-1a_human  VCLAG.....  .GPPSITDFQ  ILENQA....  ......
IL-1a_mouse  VHLAR.....  .GLPSMTDFQ  IS........  ......
IL-1g_human  LILKKEDE..  .LGDRSIMFT  VQNED.....  ......
IL-1g_mouse  LILKKKDE..  .NCDKSVMFT  LTNLHQS...  ......
IL-1b_human  VFLGGTK...  .GGQDITDFT  MQPVSS....  ......
IL-1b_mouse  VFLGNNS...  ..GQDIIDFT  MESVSS....  ......
IL-1x_human  VSLTNMPD..  .EGVMVTKFY  FQEDE.....  ......
IL-1x_mouse  VSLTNTPE..  .EPLIVTKPY  FQEDQ.....  ......
IL-1d_mouse  VRLTQIPEDP  AWDAPITDFY  FQQCD.....  ......
IL-1z_human  VGVTDKFE..  ...NRKHIEFS  FQPVCKAEMS  PSEVSD
IL-1e_mouse  LILTQELG..  ..EIFITDFE  MIVVH.....  ......
IL-1e_human  IILTSELG..  ...KSYNTAFE  LNIND.....  ......
```

IL-1a_human is SEQ ID NO: 5; IL-1a_mouse is SEQ ID NO: 6; IL-1g_human is SEQ ID NO: 7; IL-1g_mouse is SEQ ID NO: 8; IL-1b_human is SEQ ID NO: 9; IL-1b_mouse is SEQ ID NO: 10; IL-1x human (IL-1RA) is SEQ ID NO: 11; IL-1x_mouse (IL-1RA) is SEQ ID NO: 12; IL-1d_mouse is SEQ ID NO: 13; IL-1e_mouse is SEQ ID NO: 14; and IL-1e_human is SEQ ID NO: 15.

TABLE 3

Relationship between various IL-1 family members, % identity for proteins:

|      | h1a | m1a | h1b | m1b | h1RA | m1RA | h1g | m1g | h1e | m1e | m1d | h1z |
|------|-----|-----|-----|-----|------|------|-----|-----|-----|-----|-----|-----|
| h1a  |     |     |     |     |      |      |     |     |     |     |     |     |
| m1a  | 54  |     |     |     |      |      |     |     |     |     |     |     |
| h1b  | 21  | 20  |     |     |      |      |     |     |     |     |     |     |
| m1b  | 20  | 20  | 78  |     |      |      |     |     |     |     |     |     |
| h1RA | 18  | 16  | 25  | 26  |      |      |     |     |     |     |     |     |
| m1RA | 21  | 18  | 27  | 29  | 77   |      |     |     |     |     |     |     |
| h1g  | 13  | 16  | 15  | 16  | 18   | 17   |     |     |     |     |     |     |
| m1g  | 15  | 17  | 15  | 15  | 15   | 15   | 63  |     |     |     |     |     |
| h1e  | 17  | 16  | 21  | 18  | 30   | 29   | 14  | 12  |     |     |     |     |
| m1e  | 18  | 16  | 22  | 22  | 25   | 27   | 15  | 16  | 46  |     |     |     |

TABLE 3-continued

Relationship between various IL-1 family members, % identity for proteins:

|     | h1a | m1a | h1b | m1b | h1RA | m1RA | h1g | m1g | h1e | m1e | m1d | h1z |
|-----|-----|-----|-----|-----|------|------|-----|-----|-----|-----|-----|-----|
| m1d | 20  | 19  | 26  | 27  | 45   | 45   | 15  | 13  | 28  | 28  |     |     |
| h1z | 13  | 20  | 22  | 24  | 26   | 28   | 11  | 13  | 22  | 18  | 20  |     |

Comparison of the sequences will also provide an evolutionary tree. This can be generated, e.g., using the TreeView program in combination with the ClustalX analysis software program. See Thompson, et al. Nuc. Acids Res. 25: 4876–4882; and TreeView, Page, IBLS, University of Glasgow, e-mail rpage@bio.gla.ac.uk; http://taxonomy.zoology.gla.ac.uk.rod.treeview.html.

β conformation boundaries for IL-1ζ (SEQ ID NO: 2) are approximately: β1 lys58-asp64; β2 val69-ser74; β3 asn76-val80; β4 phe91-ser96; β5 ser107-val113; β6 phe118-lys126; β7 pro131-lys136; β8 phe154-val161; β9 ser163-ser169; β10 phe176-ser180; β11 glu185-gln204; and β12 phe201-gln204. The presence of amino acid residues between β conformations β4 and β5 are characteristic of IL-1 agonists. IL-1 family molecules have highly conserved residues in the region encompassing β conformations β9 and β10. Segments beginning or ending at these boundaries will be particularly interesting.

Various sites for interaction with receptor are: Site A includes residues corresponding to positions of SEQ ID NO: 2 numbered 63-66, 72-74, 78, 80-87, 181-186, and 202 and 204; Site B includes residues corresponding to positions numbered 53-56, 58, 95-103, 159, 161-164, 205, and 207; and Site C includes residues corresponding to positions numbered 127-153. See, e.g., U.S. Ser. No. 09/097,976, which is incorporated herein by reference.

As used herein, the term IL-L1ζ shall be used to describe a protein comprising a protein or peptide segment having or sharing an amino acid sequence shown in Table 1, or a substantial fragment thereof. The invention also includes protein variations of the IL-L1ζ allele whose sequence is provided, e.g., a mutein agonist or antagonist. Typically, such agonists or antagonists will exhibit less than about 10% sequence differences, and thus will often have between 1- and 11-fold substitutions, e.g., 2-, 3-, 5-, 7-fold, and others. It also encompasses allelic and other variants, e.g., natural polymorphic variants, of the protein described. "Natural" as used herein means unmodified by artifice. Typically, it will bind to its corresponding biological receptor with high affinity, e.g., at least about 100 nM, usually better than about 30 nM, preferably better than about 10 nM, and more preferably at better than about 3 nM. The term shall also be used herein to refer to related naturally occurring forms, e.g., alleles, polymorphic variants, and metabolic variants of the mammalian protein.

This invention also encompasses proteins or peptides having substantial amino acid sequence homology with the amino acid sequences in Table 1. It will include sequence variants with relatively few substitutions, e.g., typically less than about 3-5.

A substantial polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., 35, 40, 45, 50, 60, 70, 80, etc. Sequences of segments of different proteins can be compared to one another over appropriate length stretches.

Amino acid sequence homology, or sequence identity, is determined by optimizing residue matches, if necessary, by introducing gaps as required. See, e.g., Needleham, et al., (1970) J. Mol. Biol. 48:443-453; Sankoff, et al. (1983) chapter one in Time Warps, String Edits, and Macromolecules: The Theory and Practice of Sequence Comparison, Addison-Wesley, Reading, Mass.; and software packages from Intelli-Genetics, Mountain View, Calif.; and the University of Wisconsin Genetics Computer Group (GCG), Madison, Wis.; each of which is incorporated herein by reference. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural allelic and interspecies variations in the cytokine sequence. Typical homologous proteins or peptides will have from 50-100% homology (if gaps can be introduced), to 60-100% homology (if conservative substitutions are included) with an amino acid sequence segments of Table 1. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length of the compared segments. Homologous proteins or peptides, such as the allelic variants, will share most biological activities with the embodiments described in Table 1. As used herein, the term "biological activity" is used to describe, without limitation, effects on inflammatory responses and/or innate immunity. For example, it may, like IL-1γ, exhibit synergistic induction by splenocytes of IFN-γ in combination with IL-12 or IL-2, with or without anti-type I or anti-type II IL-1 receptor antibodies, or more structural properties as receptor binding and cross-reactivity with antibodies raised against the same or a polymorphic variant of a mammalian IL-1ζ.

The terms ligand, agonist, antagonist, and analog of, e.g., IL-1ζ, include molecules that modulate the characteristic cellular responses to IL-1ζ or IL-1ζ-like proteins, as well as molecules possessing the more standard structural binding competition features of ligand-receptor interactions, e.g., where the receptor is a natural receptor or an antibody. The cellular responses likely are mediated through binding of IL-1ζ to cellular receptors related to, but possibly distinct from, the type I or type II IL-1 receptors. Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds. 1990) *Goodman & Gilman's: The Pharmacological Bases of Therapeutics*, Pergamon Press, New York.

Rational drug design may also be based upon structural studies of the molecular shapes of a receptor or antibody and other effectors or ligands. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

II. Activities

The IL-1ζ polypeptides will have a number of different biological activities, e.g., in the immune system, and will include inflammatory functions or other innate immunity responses. The IL-1ζ polypeptides are homologous to other IL-1 proteins, but each have structural differences. For example, a human IL-1γ gene coding sequence probably has about 70% identity with the nucleotide coding sequence of mouse IL-1γ, and similar measures of similarity will likely apply to the IL-1ζ. At the amino acid level, there is also likely to be about 60% identity. This level of similarity suggests that the new IL-1ζ proteins are related to the other IL-1α, IL-1β, IL-1RA, IL-1γ, IL-1δ, and IL-1ε.

The mouse IL-1γ molecule has the ability to stimulate IFN-γ production which augments NK activity in spleen cells. See Okamura, et al. (1995) *Nature* 378:88-91.

The activities of the mouse IL-1α, IL-1β, and IL-1γ have been compared as to their ability to induce IFN-γ, alone or in combination with IL-2 or IL-12 in SCID splenocytes and purified NK cells. See Hunter, et al. (1995) *J. Immunol.* 155: 4347-4354; and Bancroft, et al. (1991) *Immunol. Revs.* 124: 5-24. The IL-1γ was found to be much more potent in stimulating IFN-1γ than either IL-1α or IL-1β. IL-1ζ and agonists or antagonists should have related activities to these or to the other new IL-1δ and IL-1ε, typically affecting similar immune functions, including inflammatory responses.

In IL-2 activated NK cells, IFN-γ production is blocked by the addition of anti-IL-1β antibodies. See Hunter, et al. (1995). However, mouse IL-1γ can overcome this block and induce IFN-γ. This is the only cytokine known to be able to do this. In addition, in vivo, administration of mouse IL-1γ to mice infected with the parasite *T. Cruzi* significantly decreases parasitemia.

The present disclosure also describes new assays for activities predicted for the IL-1ζ molecules. Corresponding activities should be found in other mammalian systems, including primates or rodents. It is likely that the new primate IL-1-like molecules produced by similar recombinant means to the human IL-1γ protein should exhibit a biological activity of modulating lymphocyte cells in production of IFN-γ. See assays described, e.g., in de Waal Malefyt, et al., in de Vries and de Waal Malefyt (eds. 1995) "Interleukin-10" Landes Co., Austin, Tex. Furthermore, there is substantial likelihood of synergy with other IL-1 or IL-12 related agonists or antagonists. It is likely that the receptors, which are expected to include multiple different polypeptide chains, exhibit species specificity for their corresponding ligands. The IL-1α and IL-1β ligands both signal through heterodimeric receptors.

III. Nucleic Acids

This invention contemplates use of isolated nucleic acid or fragments, e.g., which encode this or a closely related protein, or fragments thereof, e.g., to encode a biologically active corresponding polypeptide. The term "isolated nucleic acid or fragments" as used herein means a nucleic acid, e.g., a DNA or RNA molecule, that is not immediately contiguous when present in the naturally occurring genome of the organism from which it is derived. Thus, the term describes, e.g., a nucleic acid that is incorporated into a vector, such as a plasmid or viral vector; a nucleic acid that is incorporated into the genome of a heterologous cell (or the genome of homologous cell, but at a site different from that at which it normally occurs); and a nucleic acid that exists as a separate molecule, e.g., a DNA fragment produced by PCR amplification or restriction enzyme digestion, or an RNA molecule produced by in vitro transcription. The term also describes a recombinant (i.e., genetically engineered) nucleic acid that forms part of a hybrid gene encoding additional polypeptide sequences that can be used, e.g., in the production of a fusion protein. In addition, this invention embodies virtually any engineered or nucleic acid molecule created by artifice that encodes a biologically active protein or polypeptide having characteristic IL-1ζ activity.

Typically, the nucleic acid is capable of hybridizing, under appropriate conditions, with a nucleic acid sequence segment shown in Table 1. Said biologically active protein or polypeptide can be a full length protein, or fragment, and will typically have a segment of amino acid sequence highly homologous to one shown in Table 1. Further, this invention covers the use of isolated or recombinant nucleic acid, or fragments thereof, which encode proteins having fragments which are homologous to the newly disclosed IL-1-like proteins. The isolated nucleic acids can have the respective regulatory sequences in the 5' and 3' flanks, e.g., promoters, enhancers, poly-A addition signals, and others from the natural gene.

An "isolated" nucleic acid is a nucleic acid, e.g., an RNA, DNA, or a mixed polymer, which is substantially pure, e.g., separated from other components which naturally accompany a native sequence, such as ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, e.g., products made by transforming cells with an unnaturally occurring vector is encompassed, as are nucleic acids comprising sequence derived using a synthetic oligonucleotide process. Such a process is often done to replace a codon with a redundant codon encoding the same or a conservative amino acid, while typically introducing or removing a restriction enzyme sequence recognition site. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. This will include a dimeric repeat. Specifically included are synthetic nucleic acids which, by genetic code redundancy, encode similar polypeptides to fragments of the IL-1ζ and fusions of sequences from various different interleukin or related molecules, e.g., growth factors.

A "fragment" in a nucleic acid context is a contiguous segment of at least about 17 nucleotides, generally at least 21 nucleotides, more generally at least 25 nucleotides, ordinarily at least 30 nucleotides, more ordinarily at least 35 nucleotides, often at least 39 nucleotides, more often at least 45 nucleotides, typically at least 50 nucleotides, more typically at least 55 nucleotides, usually at least 60 nucleotides, more usually at least 66 nucleotides, preferably at least 72 nucleotides, more preferably at least 79 nucleotides, and in particularly preferred embodiments will be at least 85 or more nucleotides including, e.g., 100, 150, 200, 250, etc. Preferred embodiments will exhibit a plurality of distinct, e.g., nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12. Typically, fragments of different genetic sequences can be compared to one another over appropriate length stretches, particularly defined segments such as the domains described below.

A nucleic acid which codes for an IL-1ζ will be particularly useful to identify genes, mRNA, and cDNA species which code for itself or closely related proteins, as well as DNAs which code for polymorphic, allelic, or other genetic variants, e.g., from different individuals or related species. Preferred probes for such screens are those regions of the interleukin which are conserved between different polymorphic variants or which contain nucleotides which lack specificity, and will preferably be full length or nearly so. In other situations, polymorphic variant specific sequences will be more useful.

This invention further covers recombinant nucleic acid molecules and fragments having a nucleic acid sequence identical to or highly homologous to the isolated DNA set forth herein. In particular, the sequences will often be operably linked to DNA segments which control transcription, translation, and DNA replication. These additional segments typically assist in expression of the desired nucleic acid segment.

Homologous nucleic acid sequences, when compared to one another or Table 1 sequences, exhibit significant similarity. The standards for homology in nucleic acids are either measures for homology generally used in the art by sequence comparison or based upon hybridization conditions. Comparative hybridization conditions are described in greater detail below.

Substantial identity in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides, including, e.g., segments encoding structural domains such as the segments described below. Alternatively, substantial identity will exist when the segments will hybridize under selective hybridization conditions, to a strand or its complement, typically using a sequence derived from Table 1. Typically, selective hybridization will occur when there is at least about 55% homology over a stretch of at least about 14 nucleotides, more typically at least about 65%, preferably at least about 75%, and more preferably at least about 90%. See, Kanehisa (1984) *Nuc. Acids Res.* 12:203-213. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needlman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403-410. Software for performing BLAST analyses is publicly available through the National Center for Biotechnology Information (http:www.ncbi.n1m.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 500 mM, usually less than about 400 mM, more usually less than about 300 mM, typically less than about 200 mM, preferably less than about 100 mM, and more preferably less than about 80 mM, even down to less than about 20 mM. However, the combination of parameters is much more important than the measure of any single parameter. See, e.g., Wetmur and Davidson (1968) *J. Mol. Biol.* 31:349-370, which is hereby incorporated herein by reference. Hybridization under stringent conditions should give a background of at least 2-fold over background, preferably at least 3-5 or more.

The isolated DNA can be readily modified by nucleotide substitutions, nucleotide deletions, nucleotide insertions, and inversions of nucleotide stretches. These modifications result in novel DNA sequences which encode this protein or its derivatives. These modified sequences can be used to produce mutant proteins (muteins) or to enhance the expression of variant species. Enhanced expression may involve gene amplification, increased transcription, increased translation, and other mechanisms. Such mutant IL-1-like derivatives include predetermined or site-specific mutations of the protein or its fragments, including silent mutations using genetic code degeneracy. "Mutant IL-1ζ" as used herein encompasses a polypeptide otherwise falling within the homology definition of the IL-1ζ as set forth above, but having an amino acid sequence which differs from that of other IL-1-like proteins as found in nature, whether by way of deletion, substitution, or insertion. In particular, "site specific mutant IL-1ζ" encompasses a protein having substantial homology with a protein of Table 1, and typically shares most of the biological activities of the form disclosed herein.

Although site specific mutation sites are predetermined, mutants need not be site specific. Mammalian IL-1ζ mutagenesis can be achieved by making amino acid insertions or deletions in the gene, coupled with expression. Substitutions, deletions, insertions, or combinations may be generated to arrive at a final construct. Insertions include amino- or carboxy-terminal fusions. Random mutagenesis can be conducted at a target codon and the expressed mammalian IL-1ζ mutants can then be screened for the desired activity. Methods for making substitution mutations at predetermined sites in DNA having a known sequence are well known in the art, e.g., by M13 primer mutagenesis. See also Sambrook, et al. (1989) and Ausubel, et al. (1987 and periodic Supplements).

The mutations in the DNA normally should not place coding sequences out of reading frames and preferably will not create complementary regions that could hybridize to produce secondary mRNA structure such as loops or hairpins.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Polymerase chain reaction (PCR) techniques can often be applied in mutagenesis. Alternatively, mutagenesis primers are commonly used methods for generating defined mutations at predetermined sites. See, e.g., Innis, et al. (eds. 1990) *PCR Protocols: A Guide to Methods and Applications* Academic Press, San Diego, Calif.; and Dieffenbach and Dveksler (1995; eds.) *PCR Primer: A Laboratory Manual* Cold Spring Harbor Press, CSH, NY.

IV. Proteins, Peptides

As described above, the present invention encompasses mammalian IL-1ζ, e.g., whose sequences are disclosed in Table 1, and described above. Allelic and other variants are also contemplated, including, e.g., fusion proteins combining portions of such sequences with others, including epitope tags and functional domains.

The present invention also provides recombinant proteins, e.g., heterologous fusion proteins using segments from these rodent proteins. A heterologous fusion protein is a fusion of proteins or segments which are naturally not normally fused in the same manner. Thus, the fusion product of a growth factor with an interleukin is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional or structural domains from other related proteins, e.g., growth factors or other cytokines. For example, receptor-binding or other segments may be "swapped" between different new fusion polypeptides or fragments. See, e.g., Cunningham, et al. (1989) *Science* 243:1330-1336; and O'Dowd, et al. (1988) *J. Biol. Chem.* 263:15985-15992, each of which is incorporated herein by reference. Thus, new chimeric polypeptides exhibiting new combinations of specificities will result from the functional linkage of receptor-binding specificities. For example, the receptor binding domains from other related ligand molecules may be added or substituted for other domains of this or related proteins. The resulting protein will often have hybrid function and properties. For example, a fusion protein may include a targeting domain which may serve to provide sequestering of the fusion protein to a particular organ, e.g., a ligand portions which is specifically bound by spleen cells and would serve to accumulate in the spleen.

Candidate fusion partners and sequences can be selected from various sequence data bases, e.g., GenBank, c/o NCBI; and BCG, University of Wisconsin Biotechnology Computing Group, Madison, Wis., which are each incorporated herein by reference.

The present invention particularly provides muteins which act as agonists or antagonists of the IL-1ζ. Structural alignment of primate IL-1ζ and other members of the IL-1 family show conserved features/residues, particularly 12 β strands folded into a β-trefoil fold. The 12 IL-1ζ β strand domains are recited, respectively, about: β1 lys58-asp64; β2 val69-ser74; β3 asn76-val80; β4 phe91-ser96; β5 ser107-val113; β6 phe118-lys126; β7 pro131-lys136; β8 phe154-val161; β9 ser163-ser169; β10 phe176-ser180; β11 glu185-gln204; and β12 phe201-gln204. The presence of amino acid residues between β conformations β4 and β5 are characteristic of IL-1 agonists. IL-1 family molecules have highly conserved residues in the region encompassing β conformations β9 and β10.

Alignment of the primate IL-1ζ with other members of the IL-1 family indicates that the β conformations correspond to similar sequences in other IL-1 family members. See also, Bazan, et al. (1996) *Nature* 379:591; Lodi, et al. (1994) *Science* 263:1762-1766; Sayle and Milner-White (1995) *TIBS* 20:374-376; and Gronenberg, et al. (1991) *Protein Engineering* 4:263-269.

The IL-1α and IL-1β ligands bind an IL-1 receptor type I as the primary receptor and this complex then forms a high affinity receptor complex with the IL-1 receptor type III. Such receptor subunits are probably shared with the new IL-1 family members.

The mouse IL-1γ does not bind to the known mouse IL-1 receptor types I, II (decoy receptor), or III. In addition, the mouse IGIF biological activity cannot be blocked with anti-type I, II, or III antibodies. This suggests that the related mouse IGIF binds to receptors related to the IL-1 receptors already isolated, but not yet identified as receptors for the IGIF.

The solved structures for IL-1β, the natural IL-1 receptor antagonist (IL-1Ra), and a co-structure of IL-1Ra/IL-1 receptor type I, however, suggest how to make a primate antagonist for IL-1ζ (see, e.g., accession numbers: U65590, gbU19844, gbU19845, gi2173679, gi2170133, gi2172939, gbM15300, gbM28983, gbU65590, gbM74294, embX04964, gi2169698, gi2169368 emb270047, gi914939, gi220782, embX52731, embX56972 and embX12497, for various species examples of IL-1 family members). Structural analyses of the mature primate IL-1ζ suggest that its β-trefoil structures contact the IL-1 receptor over three binding sites (designated A, B and C). Sites A and C bind to the first receptor subunit (alpha) of IL-1 while site B binds the IL-1 second receptor subunit (beta). Homology sequence comparison of the IL-1 family members reveals that the only known antagonist to IL-1 receptor (IL-1x, or IL-1RA; Table 2) is missing an amino acid domain bounded by the β4 and β5 strands. This domain maps to a portion of site B in primate IL-1ζ (Table 2) that binds to the IL-1 second receptor subunit, suggesting that its absence confers antagonist activity as evidenced by homology comparison among other IL-1 family members. This loop portion of contact site B spans approximately 7-10 amino residues, while in IL-1RA the loop is "cut off" with only 2 residues remaining. Therefore, IL-1RA binds normally to receptor type I, but cannot interact with receptor type III. This makes IL-1RA into an effective IL-1 antagonist.

The corresponding location in primate IL-1ζ (between β4 and β5) defines a domain that forms a polypeptide loop which is part of a primary binding segment to the IL-1 receptor type. The loop is defined, for IL-1ζ, approximately by amino residues ser100-gly106 of SEQ ID NO: 2. Accordingly, IL-1ζ antagonist activity should be generated by removal all or an appropriate portion of a corresponding portion of amino acids located between β4 and β5. This suggests that analogous modifications to the loop between the β4 and the β5 strands will lead to variants with predictable biological activities. With mouse IL-1RA, it was shown that replacement of the mouse IL-1RA residues with those mouse IL-1β residues introduced IL-1 activity to the IL-1RA variant (IL-1RA could then bind type III receptor). Similar substitutions should establish that type III receptor can probably be used by primate IL-1ζ or muteins.

Sites A and C should mediate binding of IL-1ζ to the first IL-1 receptor subunit, e.g., an alpha receptor subunit. Site A contacts correspond in IL-1ζ to amino residues corresponding to positions of SEQ ID NO: 2 numbered about 63-66, 72-74, 78, 80-87, 181-186, and 202 and 204; Site B includes residues corresponding to positions numbered about 53-56, 58, 95-103, 159, 161-164, 205, and 207; and Site C includes residues corresponding to positions numbered about 127-153. See, e.g., U.S. Ser. No. 09/097,976, which is incorporated herein by reference.

Similar variations in other species counterparts of IL-1ζ ligand sequence, e.g., in the corresponding regions, should provide similar interactions with receptor. Substitutions with either mouse sequences or human sequences are indicated.

Conversely, conservative substitutions away from the receptor binding interaction regions will probably preserve most biological activities.

"Derivatives" of the mammalian IL-1ζ include amino acid sequence mutants, glycosylation variants, metabolic derivatives and covalent or aggregative conjugates with other chemical moieties. Covalent derivatives can be prepared by linkage of functionality's to groups which are found in the IL-1ζ amino acid side chains or at the N- or C-termini, e.g., by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the interleukin or fragments thereof with other proteins of polypeptides. These derivatives can be synthesized in recombinant culture such as N— or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the interleukin and other homologous or heterologous proteins are also provided. Homologous polypeptides may be fusions between different growth factors, resulting in, for instance, a hybrid protein exhibiting ligand specificity for multiple different receptors, or a ligand which may have broadened or weakened specificity of binding to its receptor. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include glutathione-S-transferase (GST), bacterial β-galactosidase, trpE, Protein A, β-lactamase, alpha amylase, alcohol dehydrogenase, and yeast alpha mating factor. See, e.g., Godowski, et al. (1988) *Science* 241:812-816.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), Vols. 1-3, Cold Spring Harbor Laboratory, and Ausubel, et al. (eds. 1987 and periodic supplements) *Current Protocols in Molecular Biology*, Greene/Wiley, New York, which are each incorporated herein by reference. Techniques for synthesis of polypeptides are described, e.g., in Merrifield (1963) *J. Amer. Chem. Soc.* 85:2149-2156; Merrifield (1986) *Science* 232: 341-347; and Atherton, et al. (1989) *Solid Phase Peptide Synthesis: A Practical Approach*, IRL Press, Oxford; each of which is incorporated herein by reference. See also, Dawson, et al. (1994) *Science* 266:776-779 for methods to make larger polypeptides.

In another embodiment, the present invention relates to substantially purified peptide fragments of IL-1ζ that block binding between IL-1 family members and a target receptor. Such peptide fragments could represent research and diagnostic tools in the study of inflammatory reactions to antigenic challenge and the development of more effective anti-inflammatory therapeutics. In addition, pharmaceutical compositions comprising isolated and purified peptide fragments of IL-1ζ may represent effective anti-inflammatory therapeutics.

The term "substantially purified" as used herein refers to a molecule, such as a peptide that is substantially free of other proteins, lipids, carbohydrates, nucleic acids, or other biological materials with which it is naturally associated. For example, a substantially pure molecule, such as a polypeptide, can be at least 60%, by dry weight, the molecule of interest. One skilled in the art can purify IL-1ζ peptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

The invention relates not only to fragments of naturally-occurring IL-1ζ, but also to IL-1ζ mutants and chemically synthesized derivatives of IL-1ζ that block binding between IL-1 family members and a target receptor.

For example, changes in the amino acid sequence of IL-1ζ are contemplated in the present invention. IL-1ζ can be altered by changing the nucleic acid sequence encoding the protein. Preferably, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Additionally, other variants and fragments of IL-1ζ can be used in the present invention. Variants include analogs, homologues, derivatives, muteins, and mimetics of IL-1ζ that retain the ability to block binding between IL-1ζ family members and a target receptor. Fragments of the IL-1ζ refer to portions of the amino acid sequence of IL-1ζ as defined in SEQ ID NO: 2 that also retain this ability. The variants and fragments can be generated directly from IL-1ζ itself by chemical modification, by proteolytic enzyme digestion, or by combinations thereof. Additionally, genetic engineering techniques, as well as methods of synthesizing polypeptides directly from amino acid residues, can be employed.

Non-peptide compounds that mimic the binding and function of IL-1ζ ("mimetics") can be produced by the approach outlined in Saragovi, et al. (1991) *Science* 253:792-795. Mimetics are molecules which mimic elements of protein secondary structure. See, e.g., Johnson et al., "Peptide Turn Mimetics," in Pezzuto, et al. (eds. 1993) *Biotechnology and Pharmacy*, Chapman and Hall, New York. The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of IL-1ζ.

Variants and fragments also can be created by recombinant techniques employing genomic or cDNA cloning methods. Site-specific and region-directed mutagenesis techniques can be employed. See, e.g., vol. 1, ch. 8 in Ausubel, et al. (eds. 1989 and periodic updates) *Current Protocols in Molecular Biology* Wiley and Sons; and Oxender and Fox (eds.) *Protein Engineering* Liss, Inc. In addition, linker-scanning and PCR-mediated techniques can be employed for mutagenesis. See, e.g., Erlich (ed. 1989) *PCR Technology* Stockton Press. Protein sequencing, structure and modeling approaches for use with the above techniques are disclosed, e.g., in Oxender and Fox (eds.) *Protein Engineering* Liss, Inc; and Ausubel, et al. (eds. 1989 and periodic updates) *Current Protocols in Molecular Biology* Wiley and Sons.

This invention also contemplates the use of derivatives of IL-1ζ other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, e.g., with cell membranes. Such covalent or aggregative derivatives are useful as immunogens, as reagents in immunoassays, or in purification methods such as for affinity purification of a receptor or other binding molecule, e.g., an antibody. For example, an IL-1ζ ligand can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of IL-1ζ receptor, antibodies, or other similar molecules. The IL-1ζ can also be labeled with a detectable group, e.g., radio-iodinated by the chloramine T procedure, covalently bound to rare earth chelates, or conjugated to another fluorescent moiety for use in diagnostic assays.

An IL-1ζ of this invention can be used as an immunogen for the production of antisera or antibodies specific, e.g., capable of distinguishing between other IL-1 family members and an IL-1ζ, for the interleukin or fragments thereof. The purified interleukin can be used to screen monoclonal antibodies or antigen-binding fragments prepared by immunization with various forms of impure preparations containing the protein. In particular, the term "antibodies" also encompasses antigen binding fragments of natural antibodies. The purified interleukin can also be used as a reagent to detect antibodies generated in response to the presence of elevated levels of expression, or immunological disorders which lead to antibody production to the endogenous cytokine. Additionally, IL-1ζ fragments may also serve as immunogens to produce the antibodies of the present invention, as described immediately below. For example, this invention contemplates antibodies having binding affinity to or being raised against the amino acid sequence shown in Table 1, fragments thereof, or homologous peptides. In particular, this invention contemplates antibodies having binding affinity to, or having been raised against, specific fragments which are predicted to be, or actually are, exposed at the exterior protein surface of the native cytokine.

The blocking of physiological response to these interleukins may result from the inhibition of binding of the ligand to the receptor, likely through competitive inhibition. Thus, in vitro assays of the present invention will often use antibodies or ligand binding segments of these antibodies, or fragments attached to solid phase substrates. These assays will also allow for the diagnostic determination of the effects of either binding region mutations and modifications, or ligand mutations and modifications, e.g., ligand analogs.

This invention also contemplates the use of competitive drug screening assays, e.g., where neutralizing antibodies to the interleukin or fragments compete with a test compound for binding to a receptor or antibody. In this manner, the neutralizing antibodies or fragments can be used to detect the presence of a polypeptide which shares one or more binding sites to a receptor and can also be used to occupy binding sites on a receptor that might otherwise bind an interleukin.

V. Making Nucleic Acids and Protein

DNA which encodes the protein or fragments thereof can be obtained by chemical synthesis, screening cDNA libraries, or by screening genomic libraries prepared from a wide variety of cell lines or tissue samples. Natural sequences can be isolated using standard methods and the sequences provided herein, e.g., in Table 1. Other species counterparts can be identified by hybridization techniques, or by various PCR techniques, combined with or by searching in sequence databases.

This DNA can be expressed in a wide variety of host cells for the synthesis of a full-length interleukin or fragments which can in turn, e.g., be used to generate polyclonal or monoclonal antibodies; for binding studies; for construction and expression of modified agonist/antagonist molecules; and for structure/function studies. Each variant or its fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The protein, or portions thereof, may be expressed as fusions with other proteins.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes a protein, as described, or a fragment thereof encoding a biologically active equivalent polypeptide. The DNA can be under the control of a viral promoter and can encode a selection marker. This invention further contemplates use of such expression vectors which are capable of expressing eukaryotic cDNA coding for such a protein in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the interleukin protein or its fragments in various hosts using vectors that do not contain a replication origin that is recognized by the host cell. It is also possible to use vectors that cause integration of the protein encoding portion or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (eds.) *Vectors: A Survey of Molecular Cloning Vectors and Their Uses*, Butterworth, Boston, 1988, which are incorporated herein by reference.

Transformed cells are cells, preferably mammalian, that have been transformed or transfected with receptor vectors constructed using recombinant DNA techniques. Transformed host cells usually express the desired protein or its fragments, but for purposes of cloning, amplifying, and manipulating its DNA, do not need to express the subject protein. This invention further contemplates culturing transformed cells in a nutrient medium, thus permitting the interleukin to accumulate in the culture. The protein can be recovered, either from the culture or from the culture medium.

For purposes of this invention, nucleic sequences are operably linked when they are functionally related to each other. For example, DNA for a pre-sequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC-series); trp promoter (pBR322-trp); lpp promoter (the pIN-series); lambda-pp or pR promoters (pOTS); or hybrid promoters such as ptac (pDR540). See Brosius, et al. (1988) "Expression Vectors Employing Lambda-, trp-, lac-, and Ipp-derived Promoters", in *Vectors: A Survey of Molecular Cloning Vectors and Their Uses*, (eds. Rodriguez and Denhardt), Buttersworth, Boston, Chapter 10, pp. 205-236, which is incorporated herein by reference.

Lower eukaryotes, e.g., yeasts and *Dictyostelium*, may be transformed with IL-1ζ sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are normally the preferred host cells for expression of the functionally active interleukin protein. In principle, virtually any higher eukaryotic tissue culture cell line is workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136-1142; pMC1neo PolyA, see Thomas, et al. (1987) *Cell* 51:503-512; and a baculovirus vector such as pAC 373 or pAC 610.

For secreted proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g., von-Heijne (1986) *Nucleic Acids Research* 14:4683-4690, and the precise amino acid composition of the signal peptide does not appear to be critical to its function, e.g., Randall, et al. (1989) *Science* 243:1156-1159; Kaiser et al. (1987) *Science* 235:312-317.

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the interleukin gene may be co-transformed with one or more genes encoding mammalian or other glycosylating enzymes. Using this approach, certain mammalian glycosylation patterns will be achievable in prokaryote or other cells.

The source of IL-1ζ can be a eukaryotic or prokaryotic host expressing recombinant IL-1ζ DNA, such as is described above. The source can also be a cell line such as mouse Swiss 3T3 fibroblasts, but other mammalian cell lines are also contemplated by this invention, with the preferred cell line being from the human species.

Now that the entire sequence is known, the primate (human) IL-1ζ, fragments, or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; all of each which are incorporated herein by reference. For example, an azide process, an acid chloride process, an acid anhydride process, a mixed anhydride process, an active ester process (e.g., p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The IL-1ζ protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149-2156, which is incorporated herein by reference.

The prepared protein and fragments thereof can be isolated and purified from the reaction mixture by means of peptide separation, e.g., by extraction, precipitation, electrophoresis, various forms of chromatography, and the like. The interleukin of this invention can be obtained in varying degrees of purity depending upon its desired use. Purification can be accomplished by use of the protein purification techniques disclosed herein, see below, or by the use of the antibodies herein described in methods of immunoabsorbant affinity chromatography. This immunoabsorbant affinity chromatography is carried out by first linking the antibodies to a solid support and then contacting the linked antibodies with solubilized lysates of appropriate cells, lysates of other cells expressing the interleukin, or lysates or supernatants of cells producing the protein as a result of DNA techniques, see below.

Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%-99% or more. Purity will usually be on a weight basis, but can also be on a molar basis. Different assays will be applied as appropriate.

VI. Antibodies

The term "antibody" or "antibody molecule" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows: (1) Fab, the fragment which contains a monovalent antigen-binding fragment of an antibody molecule can be produced by digestion of whole IgG antibody with the enzyme papain to yield an intact light chain and a portion of one heavy chain; (2) Fab', the fragment of an antibody molecule can be obtained by treating whole IgG antibody with pepsin, followed by reduction, to yield an intact light chain and a portion of the heavy chain; two Fab' fragments are obtained per antibody molecule; (3) (Fab')$_2$, the fragment of the IgG antibody that can be obtained by treating whole antibody with the enzyme pepsin without subsequent reduction; F(ab')$_2$ is a dimer of two Fab' fragments held together by two disulfide bonds; (4) Fv, defined as a genetically engineered fragment containing essentially the variable region of the light chain and the variable region of the heavy chain expressed as two chains; and (5) Single Chain Antibody ("SCA"), defined as a genetically engineered molecule containing essentially the variable region of the light chain, the variable region of the heavy chain, linked by a suitable polypeptide linker as a genetically fused single chain molecule.

Methods of making these fragments are known in the art. See, e.g., Harlow and Lane (current edition) *Antibodies: A Laboratory Manual*, Cold Spring Harbor Laboratory, New York. Therefore, the-phrase "antibody molecule" in its various forms as used herein contemplates both an intact antibody (immunoglobulin) molecule and an immunologically active portion of an antibody (immunoglobulin) molecule. Recombinant methods may be applied to make these fragments.

The term "monoclonal antibody" refers to a population of one species of antibody molecule of antigen-specificity. A monoclonal antibody contains one species of antibody combining site capable of immunoreacting with a particular antigen and thus typically displays a single binding affinity for that antigen. A monoclonal antibody may therefore contain a bispecific antibody molecule having two antibody combining sites, each immunospecific for a different antigen. In one embodiment, the first antibody molecule is affixed to a solid support. In addition, the antibody molecules in a phage display combinatorial library are also monoclonal antibodies.

As used in this invention, the term "epitope" means an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The word "complex" as used herein refers to the product of a specific binding agent-ligand reaction. An exemplary complex is an immunoreaction product formed by an antibody-antigen reaction.

The term "antigen" refers to a polypeptide or protein that is able to selectively bind to (immunoreact with) an antibody and form an immunoreaction product (immunocomplex). The site on the antigen to which the antibody binds is referred to as an antigenic determinant or epitope, and the labeling should be detectable, e.g., 2×, 5×, or more above background.

The method of the invention for detection of antibodies that bind to novel epitopes in a sample is performed in vitro, e.g., in immunoassays in which the antibodies can be identified in liquid phase or bound to a solid phase carrier. Preferably, the method is performed with a capture antibody bound to a solid support. Preferably, the capture antibody is a monoclonal antibody molecule.

Examples of types of immunoassays which can be utilized to detect novel antibodies in a sample, include competitive and non-competitive immunoassays in either a direct or indirect format. Examples of such immunoassays are the radio-immunoassay (RIA) and the sandwich (immunometric) assay. Detection of the antibodies can be done utilizing immunoassays which are run in either the forward, reverse, or simultaneous modes, including competition immunoassays and immunohistochemical assays on physiological samples. Preferably, the method of the invention utilizes a forward immunoassay. Those of skill in the art will know, or can readily discern, other immunoassay formats without undue experimentation.

Solid phase-bound antibody molecules are bound by adsorption from an aqueous medium, although other modes of affixation, such as covalent coupling or other well known means of affixation to the solid matrix can be used. Preferably, the first antibody molecule is bound to a support before forming an immunocomplex with antigen, however, the immunocomplex can be formed prior to binding the complex to the solid support.

Non-specific protein binding sites on the surface of the solid phase support are preferably blocked. After adsorption of solid phase-bound antibodies, an aqueous solution of a protein free from interference with the assay such as bovine, horse, or other serum albumin that is also free from contamination with the antigen is admixed with the solid phase to adsorb the admixed protein onto the surface of the antibody-containing solid support at protein binding sites on the surface that are not occupied by the antibody molecule.

A typical aqueous protein solution contains about 2-10 weight percent bovine serum albumin in PBS at a pH of about 7-8. The aqueous protein solution-solid support mixture is typically maintained for a time period of at least one hour at a temperature of about 4°-37° C. and the resulting solid phase is thereafter rinsed free of unbound protein.

The first preselected antibody can be bound to many different carriers and used to detect novel epitope binding antibodies in a sample. Examples of well-known carriers include glass, polystyrene, polypropylene, polyethylene, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation.

In addition, if desirable, an antibody for detection in these immunoassays can be detectably labeled in various ways. There are many different labels and methods of labeling known to those of ordinary skill in the art. Examples of the types of labels which can be used in the present invention include enzymes, radioisotopes, fluorescent compounds, colloidal metals, chemiluminescent compounds, and bio-luminescent compounds. Those of ordinary skill in the art will know of other suitable labels for binding to the monoclonal antibodies of the invention, or will be able to ascertain such, using routine experimentation. Furthermore, the binding of these labels to the antibodies used in the method of the invention can be done using standard techniques common to those of ordinary skill in the art.

Antibodies which bind to IL-1ζ polypeptides of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, e.g., by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies. See, e.g., Coligan, et al. (current ed.) *Current Protocols in Immunology*, Wiley Interscience.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The preparation of polyclonal antibodies is well-known to those skilled in the art. See, e.g., Green, et al. "Production of Polyclonal Antisera" pages 1-5 in Manson (ed.) *Immunochemical Protocols* Humana Press; Harlow and Lane; and Coligan, et al. *Current Protocols in Immunology*.

The preparation of monoclonal antibodies likewise is conventional. See, e.g., Kohler and Milstein (1975) *Nature* 256: 495-497; Coligan, et al., sections 2.5.1-2.6.7; and Harlow and Lane *Antibodies: A Laboratory Manual*, Cold Spring Harbor Press. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al.; Barnes, et al. "Purification of Immunoglobulin G (IgG)" in *Methods in Molecular Biology*, vol. 10, pages 79-104 (Humana Press, current ed.). Methods of in vitro and in vivo multiplication of monoclonal antibodies are well-known to those skilled in the art. Multiplication in vitro may be carried out in suitable culture media such as Dulbecco's Modified Eagle Medium or RPMI 1640 medium, optionally replenished, e.g., by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications are conceivable for the antibodies of the present invention. For example, antibodies of the present invention may also be derived from subhuman primate antibody. General techniques for raising therapeutically useful antibodies in baboons may be found, e.g., in Goldenberg, et al. (1991) WO 91/11465; and Losman, et al. (1990) *Int. J. Cancer* 46:310-314.

Alternatively, a therapeutically useful anti-IL-1ζ antibody may be derived from a "humanized" monoclonal antibody. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, e.g., by Orlandi, et al. (1989) *Proc. Nat'l Acad. Sci. USA* 86:3833-3837. Techniques for producing humanized monoclonal antibodies are described, e.g., by Jones et al. (1986) *Nature* 321:522-525; Riechmann, et al. (1988) *Nature* 332:323-327; Verhoeyen, et al. (1988) *Science* 239:1534-1536; Carter, et al. (1992) *Proc. Nat'l Acad. Sci. USA* 89:4285-4289; Sandhu (1992) *Crit. Rev. Biotech.* 12:437-462; and Singer, et al. (1993) *J. Immunol.* 150: 2844-2857.

Antibodies of the invention also may be derived from human antibody fragments isolated from a combinatorial immunoglobulin library. See, e.g., Barbas, et al. (1991) *Methods: A Companion to Methods in Enzymology*, vol. 2, page 119; and Winter, et al. (1994) *Ann. Rev. Immunol.* 12:433-455. Cloning and expression vectors that are useful for producing a human immunoglobulin phage library can be obtained, e.g., from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green, et al. (1994) *Nature Genet.* 7:13; Lonberg, et al. (1994) *Nature* 368:856; and Taylor, et al. (1994) *Int. Immunol.* 6:579.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of IgG antibodies with pepsin to provide a 5 S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using papain produces two monovalent Fab fragments and an Fc fragment directly. These methods are described, e.g., by Goldenberg, U.S. Pat. No. 4,036,945 and U.S. Pat. No. 4,331,647, and references contained therein. These patents are hereby incorporated in their entireties by reference including all figures, drawings, and illustrations. See also Nisonhoff, et al. (1960) *Arch. Biochem. Biophys.* 89:230-xxx; Porter (1959) *Biochem. J.* 73:119-xxx; Edelman, et al. (1967) *Methods in Enzymology*, vol. 1, Academic Press; and Coligan, et al.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar, et al. (1972) *Proc. Nat'l Acad. Sci. USA* 69:2659. Alternatively, the variable chains can be linked by an intermolecular disulfide bond or cross-linked by chemicals such as glutaraldehyde. See, e.g., Sandhu (1992) *Crit. Rev. Biotech.* 12:437. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, e.g., by Whitlow, et al. (1991) *Methods: A Companion to Methods in Enzymology*, vol. 2, page 97; Bird, et al. (1988) *Science* 242:423-426; Ladner, et al., U.S. Pat. No. 4,946,778; Pack, et al. (1993) *Bio/Technology* 11:1271-77; and Sandhu (1992) *Crit. Rev. Biotech.* 12:437-462.

Another form of an antibody fragment is a peptide coding for a single complementarity-determining region (CDR). CDR peptides ("minimal recognition units") can be obtained by constructing genes encoding the CDR of an antibody of interest. Such genes are prepared, e.g., by using the polymerase chain reaction to synthesize the variable region from RNA of antibody-producing cells. See, e.g., Larrick, et al. (1991) *Methods: A Companion to Methods in Enzymology*, vol. 2, page 106.

Antibodies can be raised to the various mammalian, e.g., primate IL-1ζ polypeptides, both in naturally occurring native forms and in their denatured forms, the difference being that antibodies to the active ligand are more likely to recognize epitopes which are only present in the native conformations. Denatured antigen detection can also be useful in, e.g., Western analysis. Anti-idiotypic antibodies are also contemplated, which would be useful as agonists or antagonists of a natural receptor or an antibody.

A number of immunogens may be used to produce antibodies selectively reactive with IL-1ζ proteins. Recombinant protein is the preferred immunogen for the production of monoclonal or polyclonal antibodies. Naturally occurring protein may also be used either in pure or impure form. Synthetic peptides made using the IL-1ζ protein sequences described herein may also used as an immunogen for the production of antibodies to the antigens. Recombinant protein can be expressed in eukaryotic or prokaryotic cells as described herein, and purified as described. The product is then injected into an animal capable of producing antibodies. Either monoclonal or polyclonal antibodies may be generated for subsequent use in immunoassays to measure the protein.

Methods of producing polyclonal antibodies are known to those of skill in the art. In brief, an immunogen, preferably a purified protein, is mixed with an adjuvant and animals are immunized with the mixture. The animal's immune response to the immunogen preparation is monitored by taking test bleeds and determining the titer of reactivity to the protein antigen of interest. When appropriately high titers of antibody to the immunogen are obtained, blood is collected from the animal and antisera are prepared. Further fractionation of the antisera to enrich for antibodies reactive to the protein can be done if desired. See Harlow and Lane.

Monoclonal antibodies may be obtained by various techniques familiar to those skilled in the art. Briefly, spleen cells from an animal immunized with a desired antigen are immortalized, commonly by fusion with a myeloma cell. Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275-1281.

Antibodies, including binding fragments and single chain versions, against predetermined fragments of the protein can be raised by immunization of animals with conjugates of the fragments with immunogenic proteins. Monoclonal antibodies are prepared from cells secreting the desired antibody. These antibodies can be screened for binding to normal or defective protein, or screened for agonistic or antagonistic activity. These monoclonal antibodies will usually bind with at least a $K_D$ of about 1 mM, more usually at least about 300 μM, typically at least about 100 μM, more typically at least about 30 μM, preferably at least about 10 μM, and more preferably at least about 3 μM or better; including 1 μM, 300 nM, 100 nM, 30 nM, etc.

The antibodies, including antigen binding fragments, of this invention can have significant diagnostic or therapeutic value. They can be potent antagonists that bind to the interleukin and inhibit binding to the receptor or inhibit the ability of IL-1ζ to elicit a biological response. They also can be useful as non-neutralizing antibodies and can be coupled to toxins or radionuclides to bind producing cells, or cells localized to the source of the interleukin. Further, these antibodies can be conjugated to drugs or other therapeutic agents, either directly or indirectly by means of a linker.

The antibodies of this invention can also be useful in diagnostic applications. As capture or non-neutralizing antibodies, they can bind to the interleukin without inhibiting receptor binding. As neutralizing antibodies, they can be useful in competitive binding assays. They will also be useful in detecting or quantifying IL-1ζ. They may be used as reagents for Western blot analysis, or for immunoprecipitation or immunopurification of the respective protein.

Protein fragments may be joined to other materials, particularly polypeptides, as fused or covalently joined polypeptides to be used as immunogens. Mammalian IL-1ζ and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; and Williams, et al. (1967) *Methods in Immunology and Immunochemistry*, Vol. 1, Academic Press, New York; each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495-497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275-1281; and Ward, et al. (1989) *Nature* 341:544-546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant or chimeric immunoglobulins may be produced, see Cabilly, U.S. Pat. No. 4,816,567; or made in transgenic mice, see Mendez, et al. (1997) *Nature Genetics* 15:146-156. These references are incorporated herein by reference.

The antibodies of this invention can also be used for affinity chromatography in isolating the IL-1ζ. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby the purified protein will be released. The protein may be used to purify antibody.

The antibodies may also be used to screen expression libraries for particular expression products. Usually the antibodies used in such a procedure will be labeled with a moiety allowing easy detection of presence of antigen by antibody binding.

Antibodies raised against an IL-1ζ will also be used to raise anti-idiotypic antibodies. These will be useful in detecting or diagnosing various immunological conditions related to expression of the protein or cells which express receptors for the protein. They also will be useful as agonists or antagonists of the interleukin, which may be competitive inhibitors or substitutes for naturally occurring ligands.

Binding Agent: IL-1ζ Polypeptide Complex

An IL-1ζ polypeptide that specifically binds to or that is specifically immunoreactive with an antibody, e.g., such as a polyclonal antibody, generated against a defined immunogen, e.g., such as an immunogen consisting of an amino acid sequence of SEQ ID NO: 2 or fragments thereof or a polypeptide generated from the nucleic acid of SEQ ID NO: 1 is typically determined in an immunoassay. Included within the metes and bounds of the present invention are those nucleic acid sequences described herein, including functional variants, that encode polypeptides that selectively bind to polyclonal antibodies generated against the prototypical IL-1ζ polypeptide as structurally and functionally defined herein. The immunoassay typically uses a polyclonal antiserum which was raised, e.g., to a protein of SEQ ID NO: 2. This antiserum is selected to have low crossreactivity against other IL-1 family members, preferably from the same species, and such crossreactivity is removed by immunoabsorption or depletion prior to use in the immunoassay. Appropriate selective serum preparations can be isolated, and characterized.

In order to produce antisera for use in an immunoassay, the protein of SEQ ID NO: 2 is isolated as described herein. For example, recombinant protein may be produced in a mammalian cell line. An appropriate host, e.g., an inbred strain of mice such as Balb/c, is immunized with the protein of SEQ ID NO: 2 using a standard adjuvant, such as Freund's adjuvant, and a standard mouse immunization protocol (see Harlow and Lane). Alternatively, a synthetic peptide derived from the sequences disclosed herein and conjugated to a carrier protein can be used as an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other IL-1 family members, e.g., IL-1α, IL-1β, IL-1RA, IL-1γ, IL-1δ, and IL-1ε, using a competitive binding immunoassay such as the one described in Harlow and Lane, supra, at pages 570-573. Preferably at least two IL-1 family members are used in this determination in conjunction with IL-1ζ. These IL-1 family members can be produced as recombinant proteins and isolated using standard molecular biology and protein chemistry techniques as described herein. Thus, antibody preparations can be identified or produced having desired selectivity or specificity for subsets of IL-1 family members.

Immunoassays in the competitive binding format can be used for the crossreactivity determinations. For example, the protein of SEQ ID NO: 2 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein. In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 2 that is required, then the second protein is said to specifically bind to an antibody generated to the immunogen.

It is understood that this IL-1ζ polypeptide is a member of a family of homologous proteins that comprise at least 6 so far identified genes. For a particular gene product, such as the IL-1ζ, the term refers not only to the amino acid sequences disclosed herein, but also to other proteins that are allelic, non-allelic or species variants.

It also understood that the term "IL-1ζ" includes nonnatural mutations introduced by deliberate mutation using conventional recombinant technology such as single site mutation, or by excising short sections of DNA encoding the respective proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring IL-1 related protein, e.g., the IL-1ζ polypeptide shown in SEQ ID NO: 2. The biological properties of the altered proteins can be determined by expressing the protein in an appropriate cell line and measuring the appropriate effect upon lymphocytes. Particular protein modifications considered minor would include conservative substitution of amino acids with similar chemical properties, as described above for the IL-1 family as a whole. By aligning a protein optimally with the protein of SEQ ID NO: 2 and by using the conventional immunoassays described herein to determine immunoidentity, one can determine the protein compositions of the invention.

VII. Kits and Quantitation

Both naturally occurring and recombinant forms of the IL-1 like molecules of this invention are particularly useful in kits and assay methods. For example, these methods would also be applied to screening for binding activity, e.g., receptors for these proteins. Several methods of automating assays have been developed in recent years so as to permit screening of tens of thousands of compounds per year. See, e.g., a BIOMEK automated workstation, Beckman Instruments, Palo Alto, Calif., and Fodor, et al. (1991) *Science* 251:767-773, which is incorporated herein by reference. The latter describes means for testing binding by a plurality of defined polymers synthesized on a solid substrate. The development of suitable assays to screen for a receptor or agonist/antagonist homologous proteins can be greatly facilitated by the availability of large amounts of purified, soluble IL-1ζ in an active state such as is provided by this invention.

Purified IL-1ζ can be coated directly onto plates for use in the aforementioned receptor screening techniques. However, non-neutralizing antibodies to these proteins can be used as capture antibodies to immobilize the respective interleukin on the solid phase, useful, e.g., in diagnostic uses.

This invention also contemplates use of IL-1ζ polypeptides and their fusion products in a variety of diagnostic kits and methods for detecting the presence of the protein or its receptor. Alternatively, or additionally, antibodies against the molecules may be incorporated into the kits and methods. Typically the kit will have a compartment containing either a defined IL-1ζ peptide or gene segment or a reagent which recognizes one or the other. Typically, recognition reagents, in the case of peptide, would be a receptor or antibody, or in the case of a gene segment, would usually be a hybridization probe.

A preferred kit for determining the concentration of, e.g., IL-1ζ, a sample would typically comprise a labeled compound, e.g., receptor or antibody, having known binding affinity for IL-1ζ, a source of IL-1ζ (naturally occurring or recombinant) as a positive control, and a means for separating the bound from free labeled compound, e.g., a solid phase for immobilizing the IL-1ζ in the test sample. Compartments containing reagents, and instructions, will normally be provided.

Antibodies, including antigen binding fragments, specific for mammalian IL-1ζ or a peptide fragment, or receptor fragments are useful in diagnostic applications to detect the presence of elevated levels of IL-1ζ and/or its fragments. Diagnostic assays may be homogeneous (without a separation step between free reagent and antibody-antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SL-FIA) and the like. For example, unlabeled antibodies can be employed by using a second antibody which is labeled and which recognizes the antibody to IL-1ζ or to a particular fragment thereof. These assays have also been extensively discussed in the literature. See, e.g., Harlow and Lane (1988) *Antibodies: A Laboratory Manual*, CSH., and Coligan (ed. 1991 and periodic supplements) *Current Protocols In Immunology* Greene/Wiley, New York.

Anti-idiotypic antibodies may have similar use to serve as agonists or antagonists of IL-1ζ. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

The aforementioned constituents of the diagnostic assays may be used without modification or may be modified in a variety of ways. For example, labeling may be achieved by covalently or non-covalently joining a moiety which directly or indirectly provides a detectable signal. In these assays, a test compound, IL-1ζ, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The IL-1ζ can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of antibody/antigen complex by appropriate methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457-1461, and the double antibody magnetic particle separation as described in U.S. Pat. No. 4,659,678, each of which is incorporated herein by reference.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an IL-1ζ. These sequences can be used as probes for detecting levels of the IL-1ζ in patients suspected of having an immunological disorder. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97.

VIII. Therapeutic Utility

This invention provides reagents with significant therapeutic value. The IL-1ζ polypeptides (naturally occurring or recombinant), mutein agonists and antagonists, and antibodies, along with compounds identified as having binding affinity to the interleukin or its receptor or antibodies, should be useful in the treatment of conditions exhibiting abnormal expression of the interleukin. Such abnormality will typically be manifested by immunological disorders. Additionally, this invention should provide therapeutic value in various diseases or disorders associated with abnormal expression or abnormal triggering of response to the interleukin. The mouse IL-γ has been suggested to be involved in tumors, allergies, and infectious diseases, e.g., pulmonary tuberculosis, leprosy, fulminant hepatitis, and viral infections, such as HIV. The IL-1ζ or antagonist may have similar function, suggesting combination compositions with other agonists or antagonists of IL-1 family members.

T helper cells mediate effector functions in infectious, allergic, or autoimmune diseases through production of cytokines. CD4 positive T cells can be divided into Th1 and Th2 subsets on the basis of their cytokine profile upon antigen stimulation. Recently obtained evidence has shown that Th1 and Th2 cells differ in responsiveness and receptor expression for IL-1 family molecules. See, e.g., Robinson, et al. (1997) *Immunity* 7:571-581. Whereas Th1 cells respond to IL-1γ, Th2 cells respond to IL-1α. This differential responsiveness between Th1 and Th2 cells to IL-1γ and IL-1α, respectively, may have profound implications for regulation of ongoing Th cell responses. The novel IL-1 molecules described here could play a similar role in either supporting a Th1 or Th2 response, depending on the presence or absence of their cognate IL-1 receptors on the cell surface of these immune cells; e.g., IL-1RD4 (ST2) is an orphan IL-1-like receptor exclusively expressed on the Th2 subset. See, e.g., Lohning, et al. (1998) *Proc. Nat'l Acad. Sci. USA* 95:6930-6935; and U.S. Ser. No. 09/040,714, which are incorporated herein by reference.

In addition, the dendritic cell expression profile shows human IL-1γ primarily expressed in activated dendritic cells. Activated dendritic cells are also a major producer of IL-12, and it is thought that this dendritic cell produced IL-12 plays a major role in directing a Th1 type response. The combination of IL-1γ and IL-12 should be extremely potent in inducing IFN-γ, suggesting that IL-1ζ, or antagonists thereof, may have similar function. It is possible that the combination of pro-inflammatory cytokines under certain circumstances could lead to septic shock. An antagonist, mutein or antibody, could prove very useful in this situation. See Rich (ed.) *Clinical Immunology: Principles and Practice*, Mosby.

Additionally, IL-1ζ being homologous members of the IL-1 family likely play a role in modulating of local and systemic inflammatory processes (see, Durum, et al. (1986) *Ann. Rev. Immunol.* 3:253-xxx), through the enhancement of blood flow, induction of chemoattractants, and the enhancement and adherence of adhesion molecules resulting in the accumulation of inflammatory cells such as macrophages and neutrophils at the site of inflammation. Additionally, it is possible that IL-1ζ can induce fibroblast growth and may play a role in contributing to the pathogenesis of chronic inflammation, as in rheumatoid arthritis or periodontal disease.

IL-1ζ is also likely to play a role in systemic inflammatory reactions, such as fever, hypoglycemia, the acute phase response of the liver, reduced plasma iron and zinc, and increased plasma copper. A systemic reaction such as septic shock involves vasodilation, due to IL-1, most likely in combination with other cytokines, including, e.g., TNF, IFN-γ, and leukemia inhibitory factor (LIF). The newly described IL-1ζ is also likely to be similarly involved.

Recombinant IL-1ζ, mutein agonists or antagonists, or IL-1ζ antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates use of antibodies or binding fragments thereof which are not complement binding.

Receptor screening using IL-1ζ or fragments thereof can be performed to identify molecules having binding affinity to the interleukin. Subsequent biological assays can then be utilized to determine if a receptor can provide competitive binding, which can block intrinsic stimulating activity. Receptor fragments can be used as a blocker or antagonist in that it blocks the activity of IL-L1ζ. Likewise, a compound having intrinsic stimulating activity can activate the receptor and is thus an agonist in that it simulates the activity of IL-L1ζ. This invention further contemplates the therapeutic use of antibodies to IL-1ζ as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics*, 8th Ed., Pergamon Press; and *Remington's Pharmaceutical Sciences* (current ed.), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Because of the likely high affinity binding between an IL-1ζ and its receptors, low dosages of these reagents would be initially expected to be effective. And the signaling pathway suggests extremely low amounts of ligand may have effect. Thus, dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

IL-1ζ polypeptides, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in a conventional dosage formulation. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by methods well known in the art of pharmacy. See, e.g., Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds. 1993) *Pharmaceutical Dosaae Forms: Parenteral Medications* Dekker, NY; Lieberman, et al. (eds. 1990) *Pharmaceutical Dosage Forms: Tablets* Dekker, NY; and Lieberman, et al. (eds. 1990) *Pharmaceutical Dosage Forms: Disperse Systems* Dekker, NY.

Another therapeutic approach included within the invention involves direct administration of reagents or compositions by conventional administration techniques (e.g., but not restricted to local injection, inhalation, or administered systemically), to the subject with an inflammatory disorder. The reagent, formulation or composition may also be targeted to specific cells or receptors by, e.g., methods described herein. The actual dosage of reagent, formulation or composition that modulates an inflammatory disorder depends on many factors, including the size and health of an organism, however one of one of ordinary skill in the art can use the following teachings describing the methods and techniques for determining clinical dosages. See, e.g., Spilker (1984) *Guide to Clinical Studies and Developing Protocols*, Raven Press, New York; Spilker (1991) *Guide to Clinical Trials*, Raven Press, New York; Craig and Stitzel (eds. 1986) *Modern Pharmacology* 2d ed., Little, Brown, Boston; Speight (ed. 1987) *Avery's Drug Treatment: Principles and Practice of Clinical Pharmacology and Therapeutics*, 3d ed., Williams and Wilkins, Baltimore; and Tallarida, et al. (1988) *Principles in General Pharmacology*, Springer-Verlag, New York; which describe how to determine the appropriate dosage; but, generally, in the range of about between 0.5 ng/ml and 500 µg/ml inclusive final concentration are administered per day to an adult in a pharmaceutically-acceptable carrier. The therapy of this invention may be combined with or used in association with other therapeutic agents, particularly agonists or antagonists of other IL-1 family members.

IX. Receptors

The description of the IL-1ζ ligand herein provides means to identify a receptor, as described above. Such receptor should bind specifically to the IL-1ζ with reasonably high affinity. Various constructs are made available which allow either labeling of the IL-1ζ to detect its receptor. For example, directly labeling IL-1ζ, fusing onto it markers for secondary labeling, e.g., FLAG or other epitope tags, etc., will allow detection of receptor. This can be histological, as an affinity method for biochemical purification, or labeling or selection in an expression cloning approach. A two-hybrid selection system may also be applied making appropriate constructs with the available IL-1ζ sequences. See, e.g., Fields and Song (1989) *Nature* 340:245-246. Typically, a cytokine will bind to its receptor at a Kd of at least about 30 µM, preferably at least about 10 µM, and more preferably at least about 3 µM or better; including 1 µM, 300 nM, 100 nM, 30 nM, etc.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1-3, CSH Press, NY; Ausubel, et al., *Biology*, Greene Publishing Associates, Brooklyn, N.Y.; or Ausubel., et al. (1987 and Supplements) *Current Protocols in Molecular Biology*, Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Meth. Enzymol.*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, N.Y.; and Crowe, et al. (1992) *QIAexpress: The High Level Expression & Protein Purification System* QIAGEN, Inc., Chatsworth, Calif.

Computer sequence analysis is performed, e.g., using available software programs, including those from the GCG (U. Wisconsin) and GenBank sources. Public sequence databases were also used, e.g., from GenBank and others.

Many techniques applicable to IL-4, IL-10, and IL-1γ, IL-1δ, and IL-1ε may be applied to IL-1ζ, as described, e.g., in U.S. Pat. No. 5,017,691 (IL-4), U.S. Ser. No. 07/453,951 (IL-10), U.S. Ser. No. 08/110,683 (IL-10 receptor); U.S. Ser. No. 08/651,998 (IL-1γ); U.S. Ser. No. 09/062,866 or U.S. Ser. No. 09/097,976 (IL-1δ and IL-1ε), each of which is incorporated herein by reference for all purposes.

II. Amplification of IL-1ζ Fragment by PCR

There are various methods of isolating the DNA sequences encoding IL-1ζ polypeptides. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding IL-1ζ polypeptides, or probes can be designed for use in amplification techniques such as PCR, for the isolation of DNA encoding IL-1ζ polypeptides.

Various methods of amplifying target sequences, such as the polymerase chain reaction, can also be used to prepare DNA encoding IL-1ζ polypeptides. Polymerase chain reaction (PCR) technology is used to amplify such nucleic acid sequences directly from mRNA, from cDNA, and from genomic libraries or cDNA libraries. The isolated sequences encoding IL-1ζ polypeptides may also be used as templates for PCR amplification.

In PCR techniques, oligonucleotide primers complementary to two 5' regions in the DNA region to be amplified are synthesized. The polymerase chain reaction is then carried out using the two primers. See Innis, et al. (current eds.) *PCR Protocols: A Guide to Methods and Applications* Academic Press, San Diego, Calif. Primers can be selected to amplify the entire regions encoding a full-length IL-1ζ polypeptide or to amplify smaller DNA segments, as desired. Once such regions are PCR-amplified, they can be sequenced and oligonucleotide probes can be prepared from sequence obtained using standard techniques. These probes can then be used to isolate DNA's encoding IL-1ζ polypeptides.

Oligonucleotides for use as probes are chemically synthesized, e.g., according to the solid phase phosphoramidite triester method first described by Beaucage and Carruthers (1983) *Tetrahedron Lett.* 22:1859-1862, or using an automated synthesizer, as described in Needham-VanDevanter, et al. (1984) *Nucleic Acids Res.* 12:6159-6168. Purification of oligonucleotides is performed, e.g., by native acrylamide gel electrophoresis or by anion-exchange HPLC as described in Pearson and Regnier (1983) *J. Chrom.* 255: 137-149. The sequence of the synthetic oligonucleotide can be verified using the chemical degradation method of Maxam and Gilbert in Grossman and Moldave (eds. 1980) *Methods in Enzymology* 65: 499-560 Academic Press, New York.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

To identify a homologous IL-1ζ polypeptide, degenerate oligonucleotides are designed which corresponded to conserved regions among known IL-1 family members. The primers are used for polymerase chain reactions on primate genomic DNA followed by subcloning the PCR products using restriction sites placed at the 5' ends of the primers, picking individual *E. coli* colonies carrying these subcloned inserts, and using a combination of random sequencing and hybridization analysis to eliminate known IL-1 family members.

Subsequently, PCR products are gel-purified, digested with appropriate restriction enzymes, gel-purified again, and subcloned in the Bluescript vector (Stratagene, San Diego, Calif.). Bacterial colonies carrying individual subclones are picked into 96 well microtiter plates, and multiple replicas are prepared by plating the cells onto nitrocellulose. The replicate filters are hybridized to probes representing known members of the IL-1 family, and DNA is prepared from non-hybridizing colonies for sequence analysis.

Two appropriate forward and reverse primers are selected using the sequences supplied herein (see Table 1) and common knowledge. See, e.g., Innis, et al. (current eds.) *PCR Protocols: A Guide to Methods and Applications* Academic Press, San Diego, Calif.; and Dieffenbach and Dveksler (current eds.) *PCR Primer: A Laboratory Manual* Cold Spring Harbor Press, CSH, NY. RT-PCR is used on an appropriate mRNA sample selected for the presence of message to produce a cDNA, e.g., a monocyte or macrophage cell sample.

Full length clones may be isolated by hybridization of cDNA libraries from appropriate tissues pre-selected by PCR signal.

As is commonly known, PCR primers are typically designed to contain at least 15 nucleotides, e.g., 15-30 nucleotides. The design of IL-1ζ specific primers containing 21 nucleotides, e.g., that code for IL-1ζ polypeptides containing at least 6 amino acids from the IL-1ζ domains are described as follows. Other PCR primers designed to amplify other IL-1ζ polypeptide fragments are designed in a similar fashion, e.g., mutagenesis primers. Preferably, most or all of the nucleotides in such a primer encode conserved amino acids, e.g., amino residues of SEQ. ID NO: 2 or 4, including IL-1ζ-specific amino acids as described herein. For example, primers containing at least 40% IL-1ζ-conserved amino acids can be used. Such a primer, containing 21 nucleotides, can include sequences encoding at least 3/7, 4/7, 5/7, 6/7 or 7/7 IL-1ζ-conserved amino acids. Once IL-1ζ amino acids are selected as templates against which primer sequences are to be designed, the primers can be synthesized using, e.g., standard chemical methods. Due to the degeneracy of the genetic code and the bias of preferred species variants, such primers should be designed to include appropriate degenerate sequences, as can be readily determined using common knowledge.

Based on the guidelines presented above, IL-1ζ-conserved amino acid peptides can be used as templates for the design of IL-1ζ specific primers. Additional examples can be found by analysis of sequence alignments of IL-1ζ polypeptides (Table 1 and 2). Primers can be designed to amplify various structural features or domains, e.g., a 4-10 amino acid region of either IL-1ζ polypeptide that corresponds to one of the 12 β strands could be amplified using this strategy. Depending on the length of the primer, desired primers can be designed, e.g., to correspond to 4-7 consecutive amino acids of the segments. Preferred segments include, e.g., GENSGVK; EDWEKD; CCLEDPA; FVHTSR; KKFSIHD; VLVLDS; NLIAVP; FFALAS; SSASAEK; SLILLGV; FCLYCDK; PSLQLK; KLMKLAAQ; FIFYRAQ; SRNMLES; WFICTS; EPVGVT; or FSFQPVC (see SEQ ID NO: 2); or FVHTSP; SPILLGV; or SWNMLES (see SEQ ID NO: 4). Longer preferred segments include, e.g., GVKMGSEDWEKD; AGSPLEPGPSLP; SRKVKSLNPKKF; HDQDHKVLVLDS; NLIAVPDKNYIR; FALASSLSSASA; GQSHPSLQLKKE; MKLAAQKESARR; FYRAQVGSRNML; TSCNCNEPVGVT; FENRKHIEFSFQ; or PVCKAEMSPSEV (see SEQ ID NO: 2); or AVSPLEPGPSLP; SPKVKNLNPKKF; or FYRAQVGSWNML (see SEQ ID NO: 4).

As is described above, IL-1ζ primers, e.g., primers based on IL-1ζ specific peptides shown above, or portions thereof, can be used in PCR reactions to generate IL-1ζ probes which can be used in standard screening methods to identify nucleic acids encoding IL-1 family members (see e.g., Ausubel, et al., supra).

III. Tissue Distribution of IL-1ζ

Message for the gene encoding IL-1ζ has been detected in a mixture of fetal lung, testis, and B cell cDNAs. PCR has provided positive signals in cDNA libraries derived from normal colon, lung, and a marginally detectable signal from ovary. It was detectable by Northern blotting in a polyA+ sample from a colorectal adenocarcinoma.

Southern Analysis: DNA (5 µg) from a primary amplified cDNA library is digested with appropriate restriction enzymes to release the inserts, run on a 1% agarose gel and transferred to a nylon membrane (Schleicher and Schuell, Keene, N.H.).

Samples for human mRNA isolation could include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72,. activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cells CD4+CD45RO— T cells polarized 27 days in anti-CD28, IL-4, and anti IFN-γ, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); splenocytes, resting (B100); splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); natural killer (NK) 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30-1, resting (K107); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); dendritic cells (DC) 70% CD1a+, from CD34+ GM-CSF, TNFα 12 days, resting (D101); DC 70% CD1a+, from CD34+ GM-CSF, TNFα 12 days, activated with PMA and ionomycin for 1 hr (D102); DC 70% CD1a+, from CD34+ GM-CSF, TNFα 12 days, activated with PMA and ionomycin for 6 hr (D103); DC 95% CD1a+, from CD34+ GM-CSF, TNFα 12 days FACS sorted, activated with PMA and ionomycin for 1, 6 h pooled (D104); DC 95% CD14+, from CD34+ GM-CSF, TNFα 12 days FACS sorted, activated with PMA and ionomycin 1, 6 hr pooled (D105); DC CD1a+ CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); leiomyoma L11 benign tumor (X101); normal myometrium M5 (O115); malignant leiomyosarcoma GS1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male (O106); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); and tonsil inflamed, from 12 year old (X100).

Quantitative PCR using IL-1ζ specific primers on cDNA libraries showed low expression levels across libraries. No significant signal above background was detected, except for low (+), medium (++), or high (+++) relative signals were detected across libraries: mononuclear cells, activated; T cell, TH0 clone Mot 72, resting; T cell, TH0 clone Mot 72, activated; T cell, TH0 clone Mot 72, anergic; T cell, TH1 clone HY06, resting (++); T cell, TH1 clone HY06, activated (++); T cell, TH1 clone HY06, anergic; T cell, TH2 clone HY935, resting; T cell, TH2 clone HY935, activate"; T cells CD4+, TH2 polarized, activated; T cell lines Jurkat and Hut78, resting; T cell clones, pooled, resting; T cell γδ clones, resting (+); CD28− T cell clone in pME (+); TR1 (Treg1) T cell clone (++); splenocytes, resting; splenocytes, activated; B cell EBV lines, resting; B cell line JY, activated; NK 20 clones pooled, resting (+); NK 20 clones pooled, activated; NK cytotoxic clone, resting (+++); hematopoietic precursor line TF1, activated; U937 premonocytic line, resting; U937 premonocytic line, activated; monocytes, LPS, IFNγ, anti-IL-10; monocytes, LPS, IFNγ, IL-10; monocytes, LPS, IFNγ, anti-IL-10, 4+16 h (+); monocytes, LPS, IFNγ, IL-10, 4+16 h; monocytes, LPS, 1 h; monocytes, LPS, 6 h; DC 70% CD1a+, from CD34+ GM-CSF, TNFα, resting; DC 70% CD1a+, from CD34+ GM-CSF, TNFα, activated 1 h; DC 70% CD1a+, from CD34+ GM-CSF, TNFα, activated 6 h; DC 95% CD1a+, from CD34+ GM-CSF, TNFα, activated 1+6 h; DC 95% CD14+, from CD34+ GM-CSF, TNFα, activated 1+6 h; DC CD1a+ CD86+, from CD34+ GM-CSF, TNFα, activated 1+6 h; DC ex monocytes GM-CSF, IL-4, resting; DC from monocytes GM-CSF, IL-4, resting; DC from monocytes GM-CSF, IL-4, LPS activated 4+16 h; DC from monocytes GM-CSF, IL-4, monokine activated 4+16 h; epithelial cells, unstimulated; epithelial cells, IL-1β activated; lung fibroblast sarcoma line MRC5, activated; kidney epithelial carcinoma cell line CHA, activated; normal w.t. monkey lung; *Ascaris*-challenged monkey lung, 4 h; *Ascaris*-challenged monkey lung, 24 h; pool of two normal human lung samples; pool of three heavy smoker human lung samples; allergic lung sample; Pneumocystic carnii pneumonia lung sample; normal w.t. monkey colon; normal human colon; ulcerative colitis human colon sample; normal human thyroid; Hashimoto's thyroiditis thyroid sample; pool of rheumatoid arthritis samples, human; normal human skin (+++); psoriasis patient skin sample (+++); tonsil inflamed; kidney fetal (++); lung fetal (+); liver fetal; heart fetal; brain fetal; gallbladder fetal (+); small intestine fetal (+); adipose tissue fetal; ovary fetal (+); uterus fetal; testes fetal; spleen fetal; placenta 28 wk (+); T cell, TH0 clone Mot 72,.resting; T cell, TH0 clone Mot 72, activated; T cell, TH0 clone B21, resting; T cell, TH0 clone B21, activated; T cell, TH1 clone TA20-23, resting; T cell, TH1 clone TA20-23, activated; Jurkat cell line; and genomic DNA (++). Notably, expression was detected in normal skin, which is upregulated in psoriatic skin.

Because of the elevated signal in skin, various skin derived cell samples were evaluated by quantitative PCR. While all of the signals were, in absolute terms, quite low, no significant signal above background was detected, except for low (+) or medium (++) levels in: fibroblasts IL-10 18 h (+); fibroblasts IL-10 6 h; fibroblasts IL-4 18 h; fibroblasts IL-4 6 h; fibroblasts IFNγ 18 h; fibroblasts IFNγ 6 h; fibroblasts 3d pass untreated (+); keratinocytes IL-10 18 h (++); keratinocytes IL-10 6 h (++); keratinocytes IL-4 18 h (++); keratinocytes IL-4 6 h (++); keratinocytes IFNγ 18 h (++); keratinocytes IFNγ 6 h (++); keratinocytes 3d pass untreated (++); CLA+ T cells; CLA− T cells; Langerhans cells (+); fibroblasts 7th passage (+); and keratinocytes 8th passage (+). These Langerhans and T cells were isolated from skin biopsies. In summary, the IL-1ζ message is mainly expressed by the keratinocytes, and at lower levels in fibroblasts and Langerhans cells, with no significant expression in these T cells. The expression levels are comparable to that of the other IL-1 related messages IL-1δ and IL-1ε, each at some 10-100 fold lower than levels of expression of primate IL-1α, IL-1β, or IL-1γ.

Likewise, in dendritic cells (DC), the signals were, in absolute terms, quite low. Dendritic cells (DC) are antigen-processing or presenting cells, and are found in all tissues of the body. They can be classified into various categories, including: interstitial dendritic cells of the heart, kidney, gut, and lung; Langerhans cells in the skin and mucous membranes; interdigitating dendritic cells in the thymic medula and secondary lymphoid tissue; and blood and lymph dendritic cells. For a review of dendritic cells, see Steinman (1991) *Annual Review of Immunology* 9:271-296; and Banchereau and Schmitt (eds. 1994) *Dendritic Cells in Fundamental and Clinical Immunology* Plenum Press, NY. Although dendritic cells in each of these compartments are CD45+ leukocytes that apparently arise from bone marrow, they may exhibit differences that relate to maturation state and microenvironment.

These dendritic cells again did not express large amounts of message. No significant signal above background was detected in pDC2 subset of dendritic cells (monocyte derived DC). Low message levels were detected in the DC1 (lymphocyte derived DC) day 0 and day 1 cultures. Higher levels were detected in the day 2, 3, 5, 6, 7, and 8 DC1 cultures.

Using the information described herein for cloning species variants, expression of rodent IL-1ζ can be determined as above using, e.g., a murine homologue as for a detectable probe.

IV. Cloning of Species Counterparts of IL-1ζ

Various strategies are used to obtain species counterparts of primate IL-1ζ. One method is by cross hybridization using closely related species DNA probes. The degree of identity between mouse and human IL-1 counterparts typically is as high as 70%. It may be useful to go into evolutionarily similar species as intermediate steps. Another method is by using specific PCR primers based on the identification of blocks of similarity between human and mouse IL-1 counterparts, e.g., areas of highly conserved polypeptide sequence.

In addition, the IL-1α, IL-1β, and IL-1RA genes cluster on the same human chromosome. The fourth known members of the IL-1 family, IL-1γ, which is most closely related to IL-1β, has been mapped to a different human chromosome. Duplication of the intact IL-1α, IL-1β, IL-1RA gene cluster, a potential genetic event explaining a proliferation of additional family members, would suggest the existence of two as yet unidentified IL-1 genes at the location of the IL-1γ locus. IL-1ζ is a potential candidate, and sequencing of the human IL-1γ locus may well lead to identification of the novel IL-1 genes.

V. Production of Mammalian IL-1ζ Protein

An appropriate, e.g., GST, fusion construct is engineered for expression, e.g., in *E. coli*. For example, a mouse IGIF pGex plasmid is constructed and transformed into *E. coli*. Freshly transformed cells are grown in LB medium containing 50 μg/ml ampicillin and induced with IPTG (Sigma, St. Louis, Mo.). After overnight induction, the bacteria are harvested and the pellets containing IL-1ζ are isolated. The pellets are homogenized in TE buffer (50 mM Tris-base pH 8.0, 10 mM EDTA and 2 mM pefabloc) in 2 liters. This material is passed through a microfluidizer (Microfluidics, Newton, Mass.) three times. The fluidized supernatant is spun down on a Sorvall GS-3 rotor for 1 h at 13,000 rpm. The resulting supernatant containing the IL-1ζ is filtered and passed over a glutathione-SEPHAROSE column equilibrated in 50 mM Tris-base pH 8.0. The fractions containing the IL-1ζ-GST fusion protein are pooled and cleaved with thrombin (Enzyme Research Laboratories, Inc., South Bend, Ind.). The cleaved pool is then passed over a Q-SEPHAROSE column equilibrated in 50 mM Tris-base. Fractions containing IL-1ζ are pooled and diluted in cold distilled $H_2O$, to lower the conductivity, and passed back over a fresh Q-SEPHAROSE column. Fractions containing IL-1ζ are pooled, aliquoted, and stored in the −70° C. freezer.

Alternatively, the polypeptide may be produced in a non-fusion construct and expressed. The protein may be purified, either from secreted form, or from inclusion bodies, as appropriate.

Comparison of the CD spectrum with other IL-1 family members may suggest that the protein is correctly folded. See Hazuda, et al. (1969) *J. Biol. Chem.* 264:1689-1693.

Human IL-1ζ epitope tagged protein gets secreted, e.g., from transiently transfected 293 T cells, as shown by presence of C-terminally tagged protein in the culture supernatant.

VI. Biological Assays With IL-1ζ

Biological assays confirmed IFN-γ inducing activity by IL-1γ on T cells. IL-1γ stimulates production of IFN-γ by purified NK cells, and that induction is strongly synergized with IL-12 or IL-2. Similar biological activity should be exhibited by IL-1ζ or their antagonists.

The family of interleukins 1 contains molecules, each of which is an important mediator of inflammatory disease. For a comprehensive review, see Dinarello (1996) "Biologic basis for interleukin-1 in disease" *Blood* 87:2095-2147. There are indications that the various IL-1's play important roles in the initiation of disease, including the recently identified IGIF/IL-1γ (e.g., Rothe, et al. (1997) "Active stage of autoimmune diabetes is associated with the expression of a novel cytokine, IGIF, which is located near Idd2." *J. Clin. Invest.* 99:469-474. The finding of novel proteins related to the IL-1 family furthers the identification of molecules that provide the molecular basis for initiation of disease and allow for the development of therapeutic strategies of increased range and efficacy.

Similar biological assays as applied to other known members of the family should be performed with purified IL-1ζ.

VII. Preparation of Antibodies Specific for IL-1ζ

Inbred Balb/c mice are immunized intraperitoneally with recombinant forms of the protein, e.g., purified soluble IL-1ζ-FLAG or stable transfected NIH-3T3 cells. Animals are boosted at appropriate time points with protein, with or without additional adjuvant, to further stimulate antibody production. Serum is collected, or hybridomas produced with harvested spleens.

Alternatively, Balb/c mice are immunized with cells transformed with the gene or fragments thereof, either endogenous or exogenous cells, or with isolated membranes enriched for expression of the antigen. Serum is collected at the appropriate time, typically after numerous further administrations. Various gene therapy techniques may be useful, e.g., in producing protein in situ, for generating an immune response. Operable association of heterologous promoters with natural gene sequences is also provided, as are vectors encoding the DIRS3 with a receptor partner. See, e.g., Treco, et al. WO96/29411 or U.S. Ser. No. 08/406,030.

Monoclonal antibodies may be made. For example, splenocytes are fused with an appropriate fusion partner and hybridomas are selected in growth medium by standard procedures. Hybridoma supernatants are screened for the presence of antibodies which bind to the desired IL-1ζ, e.g., by ELISA or other assay. Antibodies which specifically recognize IL-1 may also be selected or prepared, e.g., by immunoselection or related methods.

In another method, synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) *Proc. Nat'l. Acad. Sci.* 90:4156-4160; Barry, et al. (1994) *BioTechniques* 16:616-619; and Xiang, et al. (1995) *Immunity* 2: 129-135.

VIII. Production of Fusion Proteins with IL-1ζ

Various fusion constructs are made with IL-1ζ. This portion of the gene is fused to an epitope tag, e.g., a FLAG tag, or to a two hybrid system construct. See, e.g., Fields and Song (1989) *Nature* 340:245-246.

The epitope tag may be used in an expression cloning procedure with detection with anti-FLAG antibodies to detect a binding partner, e.g., receptor for the IL-1ζ. The two hybrid system may also be used to isolate proteins which specifically bind to IL-1ζ.

IX. Chromosome Mapping of IL-1ζ

Chromosome spreads are prepared. In situ hybridization is performed on chromosome preparations obtained from phytohemagglutinin-stimulated lymphocytes cultured for 72 h. 5-bromodeoxyuridine is added for the final seven hours of culture (60 µg/ml of medium), to ensure a posthybridization chromosomal banding of good quality.

An appropriate fragment, e.g., a PCR fragment, is amplified with the help of primers on total B cell cDNA template, and cloned into an appropriate vector. The vector is labeled by nick-translation with $^3$H. The radiolabeled probe is hybridized to metaphase spreads, e.g., as described in Mattei, et al. (1985) *Hum. Genet.* 69:327-331.

After coating with nuclear track emulsion (KODAK NTB$_2$), slides are exposed, e.g., for 18 days at 4° C. To avoid slipping of silver grains during the banding procedure, chromosome spreads are first stained with buffered Giemsa solution and metaphase photographed. R-banding is then performed by the fluorochrome-photolysis-Giemsa (FPG) method and metaphases rephotographed before analysis.

X. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

XI. Isolation of a Receptor for IL-1ζ

An IL-1ζ can be used as a specific binding reagent to identify its binding partner, by taking advantage of its specificity of binding, much like an antibody would be used. A binding reagent is either labeled as described above, e.g., fluorescence or otherwise, or immobilized to a substrate for panning methods.

The binding composition is used to screen an expression library made from a cell line which expresses a binding partner, i.e., receptor. Standard staining techniques are used to detect or sort intracellular or surface expressed receptor, or surface expressing transformed cells are screened by panning. Screening of intracellular expression is performed by various staining or immunofluorescence procedures. See also McMahan, et al. (1991) *EMBO J.* 10:2821-2832.

For example, on day 0, precoat 2-chamber permanox slides with 1 ml per chamber of fibronectin, 10 ng/ml in PBS, for 30 min. at room temperature. Rinse once with PBS. Then plate COS cells at 2-3×10$^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of IL-1γ-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1 M NaN$_3$ for 20 min. Cells are then washed with HBSS/saponin 1×. Add appropriate IL-1δ or IL-1δ/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85-90° C.

Evaluate positive staining of pools and progressively subclone to isolation of single genes responsible for the binding.

Alternatively, IL-1ζ reagents are used to affinity purify or sort out cells expressing a receptor. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a IL-1ζ fusion construct, or by use of antibodies raised against the first antibodies. Recursive cycles of selection and amplification lead to enrichment of appropriate clones and eventual isolation of receptor expressing clones.

Phage expression libraries can be screened by mammalian IL-1ζ. Appropriate label techniques, e.g., anti-FLAG antibodies, will allow specific labeling of appropriate clones.

All citations herein are incorporated herein by reference to the same extent as if each individual publication or patent application was specifically and individually indicated to be incorporated by reference including all figures and drawings.

Many modifications and variations of this invention, as will be apparent to one of ordinary skill in the art can be made to adapt to a particular situation, material, composition of matter, process, process step or steps, to preserve the objective, spirit and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. An isolated or purified antibody, or antigen binding fragment thereof, that specifically binds to a polypeptide consisting of the amino acid sequence of SEQ ID NO: 2 or SEQ ID NO: 4.

2. The isolated or purified antibody, or antigen binding fragment thereof, of claim 1 comprising a monoclonal antibody.

3. The isolated or purified antibody, or antigen binding fragment thereof, of claim 1 comprising a humanized antibody.

4. The isolated or purified antibody, or antigen binding fragment thereof, of claim 1 comprising a human antibody.

5. The isolated or purified antibody, or antigen binding fragment thereof, of claim 1 comprising an Fv, Fab, or F(ab')$_2$ fragment of an antibody.

6. The isolated or purified antibody, or antigen binding fragment thereof, of claim 1 further comprising a detectable label.

7. A composition comprising the isolated or purified antibody, or antigen binding fragment thereof, of claim 1 and a carrier, wherein the carrier comprises water, saline or buffer.

8. A composition comprising the isolated or purified antibody, or antigen binding fragment thereof, of claim 1 and a carrier, wherein the composition is formulated for oral, rectal, nasal, topical, or parenteral administration.

9. A kit comprising:
   a) the isolated or purified antibody, or antigen binding fragment thereof, of claim 1; and
   b) instructions for use of the antibody, or antigen binding fragment thereof.

10. A method of making the isolated or purified antibody, or antigen binding fragment thereof, of claim 1, comprising:
    a) immunizing an animal with an immunogenic amount of a polypeptide of SEQ ID NO: 2 or 4; and
    b) isolating an antibody that binds to a polypeptide comprising the amino acid sequence of SEQ ID NO: 2 or 4 from said animal after immunization.

11. A method of producing an antigen:antibody complex, comprising:
    a) contacting a polypeptide comprising the amino acid sequence of SEQ ID NO: 2 or 4 with the antibody of claim 1; and
    b) allowing the complex to form.

* * * * *